United States Patent
Stayton et al.

(10) Patent No.: US 12,329,773 B2
(45) Date of Patent: Jun. 17, 2025

(54) OXYGEN REACTIVE POLYMERS FOR TREATMENT OF TRAUMATIC BRAIN INJURY

(71) Applicant: University of Washington, Seattle, WA (US)

(72) Inventors: Patrick S. Stayton, Seattle, WA (US); Menko P. Ypma, Seattle, WA (US); Peter A. Chiarelli, Seattle, WA (US); Joshua Sang Hun Park, Seattle, WA (US); Richard G. Ellenbogen, Seattle, WA (US); Julia Mengyun Xu, Seattle, WA (US); Pierre D. Mourad, Seattle, WA (US); Donghoon Lee, Seattle, WA (US); Anthony Convertine, Seattle, WA (US); Forrest M. Kievit, Seattle, WA (US)

(73) Assignee: University of Washington, Seattle, WA (US)

( * ) Notice: Subject to any disclaimer, the term of this patent is extended or adjusted under 35 U.S.C. 154(b) by 517 days.

(21) Appl. No.: 17/379,401

(22) Filed: Jul. 19, 2021

(65) Prior Publication Data
US 2022/0152091 A1 May 19, 2022

Related U.S. Application Data

(63) Continuation of application No. 15/766,314, filed as application No. PCT/US2016/055809 on Oct. 6, 2016, now Pat. No. 11,065,272.
(Continued)

(51) Int. Cl.
*A61K 31/765* (2006.01)
*A61K 9/00* (2006.01)
(Continued)

(52) U.S. Cl.
CPC .......... *A61K 31/765* (2013.01); *A61K 9/0019* (2013.01); *A61K 9/14* (2013.01);
(Continued)

(58) Field of Classification Search
CPC ...... A61K 31/765; A61K 9/0019; A61K 9/17; A61K 9/51; A61K 31/795; A61K 47/30; A61P 25/28
See application file for complete search history.

(56) References Cited

U.S. PATENT DOCUMENTS

| 11,065,272 B2 | 7/2021 | Stayton et al. |
| 2008/0248118 A1 | 10/2008 | Labhasetwar et al. |

(Continued)

FOREIGN PATENT DOCUMENTS

| WO | 2014/106208 A1 | 7/2014 |
| WO | 2014/137741 A1 | 9/2014 |

OTHER PUBLICATIONS

Adibhatla, R.M., and J.F. Hatcher, "Lipid Oxidation and Peroxidation in CNS Health and Disease: From Molecular Mechanisms to Therapeutic Opportunities," Antioxidants & Redox Signaling 12(1):125-169, Jan. 2010.
(Continued)

*Primary Examiner* — Trevor Love
(74) *Attorney, Agent, or Firm* — Christensen O'Connor Johnson Kindness PLLC

(57) ABSTRACT

Methods and compositions for treating traumatic brain injury. The methods and compositions utilize a multi-functional oxygen reactive polymer (ORP) that includes repeating units that include a reactive oxygen species (ROS) scavenging group and a polyalkylene oxide group. For theranostic applications, the oxygen reactive polymer further includes a diagnostic group.

16 Claims, 12 Drawing Sheets

Related U.S. Application Data

(60) Provisional application No. 62/237,915, filed on Oct. 6, 2015.

(51) Int. Cl.
    *A61K 9/14*     (2006.01)
    *A61K 9/51*     (2006.01)
    *A61K 31/795*     (2006.01)
    *A61K 47/30*     (2006.01)
    *A61P 25/28*     (2006.01)

(52) U.S. Cl.
    CPC .............. *A61K 9/51* (2013.01); *A61K 31/795* (2013.01); *A61K 47/30* (2013.01); *A61P 25/28* (2018.01)

(56) References Cited

U.S. PATENT DOCUMENTS

| | | |
|---|---|---|
| 2010/0098768 A1 | 4/2010 | Andreescu et al. |
| 2010/0196481 A1 | 8/2010 | Pritchard et al. |
| 2014/0034641 A1 | 2/2014 | Akkapeddi |
| 2014/0121221 A1 | 5/2014 | Gurney et al. |

OTHER PUBLICATIONS

Albensi, B.C., et al., "Cyclosporin Ameliorates Traumatic Brain-Injury-Induced Alterations of Hippocampal Synaptic Plasticity," Experimental Neurology 162(12):385-389, Dec. 2000.
Angeloni, C., et al., "Traumatic Brain Injury and NADPH Oxidase: A Deep Relationship," Oxidative Medicine and Cellular Longevity 2015:370312, 2015, pp. 1-10.
Astete, C.E., et al., "Antioxidant Poly(lactic-co-glycolic) Acid Nanoparticles Made With R-Tocopherol Ascorbic Acid Surfactant," ACS Nano 5(12):9313-9325, Dec. 2011.
Baldwin, S.A., et al., "Blood-Brain Barrier Breach Following Cortical Contusion in the Rat," Journal of Neurosurgery 85(3):476-481, Sep. 1996.
Berguig, G.Y., et al., "Intracellular Delivery System for Antibody-Peptide Drug Conjugates," American Society of Gene & Cell Therapy 23(5):907-917, May 2015.
Bitner, B.R., et al., "Antioxidant Carbon Particles Improve Cerebrovascular Dysfunction Following Traumatic Brain Injury," ACS Nano 6(9):8007-8014, Sep. 2012.
Boyd, B.J., et al., "Traumatic Brain Injury Opens Blood-Brain Barrier to Stealth Liposomes via an Enhanced Permeability and Retention (EPR)-Like Effect," Journal of Drug Targeting 23(9):847-853, 2015.
Boyer, C., et al., "Bioapplications of RAFT Polymerization," Chemical Reviews 109(11):5402-5436, Nov. 2009.
Chen, Y., et al., "A Modified Controlled Cortical Impact Technique to Model Mild Traumatic Brain Injury Mechanics in Mice," Frontiers in Neurology 5:100, Jun. 2014, pp. 1-14.
Chu, D.S.H., et al., "Application of Living Free Radical Polymerization for Nucleic Acid Delivery," Accounts of Chemical Research 45(7):1089-1099, Jul. 2012.
Clifton, G.L., et al., "Very Early Hypothermia Induction in Patients With Severe Brain Injury (the National Acute Brain Injury Study: Hypothermia II): A Randomised Trial," The Lancet Neurology 10(2):131-139, Feb. 2011.
Clond, M.A., et al., "Reactive Oxygen Species-Activated Nanoprodug of Ibuprofen for Targeting Traumatic Brain Injury in Mice," PLOS ONE 8(4):e61819, Apr. 2013, 10 pages.
Cornelius, C., et al., "Traumatic Brain Injury: Oxidative Stress and Neuroprotection," Antioxidants & Redox Signaling 19(8):836-853, Sep. 2013.
Cruz, L.J., et al., "Effect of PLGA NP Size on Efficiency to Target Traumatic Brain Injury," Journal of Controlled Release 223:31-41, Feb. 2016.

Driessen, M.D., et al., "Proteomic Analysis of Protein Carbonylation: A Useful Tool to Unravel Nanoparticle Toxicity Mechanisms," Particle and Fibre Toxicology 12:36, Dec. 2015, pp. 1-18.
Frieden, T.R., et al., "Report to Congress: Traumatic Brain Injury in the United States: Epidemiology and Rehabilitation," submitted by Centers for Disease Control and Prevention, National Center for Injury Prevention and Control, Atlanta, GA, 2015, 72 pages.
Hall, E.D., et al., "Antioxidant Therapies for Traumatic Brain Injury," Neurotherapeutics 7(1):51-61, Jan. 2010.
Heckman, K.L., et al., "Custom Cerium Oxide Nanoparticles Protect Against a Free Radical Mediated Autoimmune Degenerative Disease in the Brain," ACS Nano 7(12):10582-10596, Dec. 2013.
Iliff, J.J., et al., "Impairment of Glymphatic Pathway Function Promotes Tau Pathology After Traumatic Brain Injury," Journal of Neuroscience 34(49):16180-16193, Dec. 2014.
Janowitz, T., and D.K. Menon, "Exploring New Routes for Neuroprotective Drug Development in Traumatic Brain Injury," Science Translational Medicine 2(27):1-10, Apr. 2010.
Jessen, N.A., et al., "The Glymphatic System: A Beginner's Guide," Neurochemical Research 40(12):2583-2599, Dec. 2015.
Kabu, S., et al., "Blast-Associated Shock Waves Result in Increased Brain Vascular Leakage and Elevated ROS Levels in a Rat Model of Traumatic Brain Injury," PLOS ONE 10(5):e0127971, May 2015, 19 pages.
Kievit, F.M., and M. Zhang, "Cancer Nanotheranostics: Improving Imaging and Therapy by Targeted Delivery Across Biological Barriers," Advanced Healthcare Materials 23(36):H217-H247, 2011.
Lane, D.D., et al., "Well-defined single polymer nanoparticles for the antibody-targeted delivery of chemotherapeutic agents," Polymeric Chemistry 6(8):1286-1299, Feb. 2015. (Author Manuscript provided, PMCID: PMC4470501, available in PMC Feb. 28, 2016, 31 pages.).
Langlois, J.A., et al., "The Epidemiology and Impact of Traumatic Brain Injury," Journal of Head Trauma Rehabilitation 21(5):375-378, 2006.
Lee, S.H., et al., "Current Progress in Reactive Oxygen Species (ROS)-Responsive Materials for Biomedical Applications," Adv Healthc Mat 2(6):908-915, 2013. (Author Manuscript provided, PMCID: PMC4146500, available in PMC Aug. 27, 2014, 15 pages.).
Lewén, A., et al., "Free Radical Pathways in CNS Injury," Journal of Neurotrauma 17(10):871-890, Oct. 2000.
Marushima, A., et al., "Newly Synthesized Radical-Containing Nanoparticles Enhance Neuroprotection After Cerebral Ischemia-Reperfusion Injury," Neurosurgery 68(5):1418-1426, May 2011.
McConeghy, K.W., et al., "A Review of Neuroprotection Pharmacology and Therapies in Patients With Acute Traumatic Brain Injury," CNS Drugs 26(7):613-636, Jul. 2012.
Miyamoto, K., et al., "Therapeutic Time Window for Edaravone Treatment of Traumatic Brain Injury in Mice," BioMed Research International 2013:379206, 2013, pp. 1-13.
Moad, G., et al., "Living Radical Polymerization by the RAFT Process—A Third Update," Australian Journal of Chemistry 65(8):985-1076, Sep. 2012.
Muthu, M.S., et al., "Nanotheranostics—Application and Further Development of Nanomedicine Strategies for Advanced Theranostics," Theranostics 4(6):660-677, Mar. 2014.
Patel, H.C., et al., "Trends in Head Injury Outcome From 1989 to 2003 and the Effect of Neurosurgical Care: An Observational Study," The Lancet 366(9496):1538-1544, Oct.-Nov. 2005.
Reddy, M.K., and V. Labhasetwar, "Nanoparticle-Mediated Delivery of Superoxide Dismutase to the Brain: An Effective Strategy to Reduce Ischemia-Reperfusion Injury," FASEB Journal 23(5):1384-1395, May 2009.
Reddy, M.K., et al., "Superoxide Dismutase-Loaded PLGA Nanoparticles Protect Cultured Human Neurons Under Oxidative Stress," Applied Biochemistry and Biotechnology 151:565-577, Dec. 2008.
Rodríguez-Rodríguez, A., et al., "Oxidative Stress in Traumatic Brain Injury," Current Medicinal Chemistry 21(10):1201-1211, Apr. 2014.
Roof, R.L., et al., "Progesterone Protects Against Lipid Peroxidation Following Traumatic Brain Injury in Rats," Molecular and Chemical Neuropathology 31(1):1-11, May 1997.

(56) References Cited

OTHER PUBLICATIONS

Roth, T.L., et al., "Transcranial Amelioration of Inflammation and Cell Death After Brain Injury," Nature 505(7482):223-228, Jan. 2014.

Roy, D., et al., "Synthesis and Characterization of Transferrin-Targeted Chemotherapeutic Delivery Systems Prepared via RAFT Copolymerization of High Molecular Weight PEG Macromonomers," Polymeric Chemistry 5(5):1791-1799, Mar. 2014. (Author Manuscript provided, PMCID: PMC4159953, available in PMC Mar. 7, 2015, 21 pages.).

Singhal, A., et al., "Nanoparticle-Mediated Catalase Delivery Protects Human Neurons From Oxidative Stress," Cell Death and Disease 4:e903, 2013, 9 pages.

Spizzirri, U.G., et al., "Synthesis of Antioxidant Polymers by Grafting of Gallic Acid and Catechin on Gelatin," Biomacromolecules 10(7):1923-1930, Jul. 2009.

Stein, D.G., "Embracing Failure: What the Phase III Progesterone Studies Can Teach About TBI Clinical Trials," Brain Injury 29(11):1259-1272, 2015.

Wan, A., et al., "Antioxidant Activity of High Molecular Weight Chitosan and N,O-Quaternized Chitosans," Journal of Agricultural and Food Chemistry 61(28):6921-6928, Jul. 2013.

Wei, J., and G.-M. Xiao, "The Neuroprotective Effects of Progesterone on Traumatic Brain Injury: Current Status and Future Prospects," Acta Pharmacologica Sinica 34(12):1485-1490, Dec. 2013.

Xiao, C., et al., "Synthesis of Thermal and Oxidation Dual Responsive Polymers for Reactive Oxygen Species (ROS)-Triggered Drug Release," Polymer Chemistry 6(5):738-747, Feb. 2015.

Xie, J., et al., "Nanoparticle-Based Theranostic Agents," Advanced Drug Delivery Reviews 62(11):1064-1079, Aug. 2010.

Xu, J., et al., "Theranostic Oxygen Reactive Polymers for Treatment of Traumatic Brain Injury," Advanced Functional Materials 26(23):4124-4133, 2016.

Muizelaar, Cerebral ischemia-reperfusion injury after severe head injury and its possible treatment with polyethyleneglycol-superoxide dismutase, 1993, Annals of Emergency Medicine, vol. 22, Issue 6, pp. 1014-1021, Abstract only (3 pages). (Year: 1993).

McKenna, Polyethylene glycol solution as an oral contrast agent for MRI of the small bowel in a patient population, 2006, Clinical Radiology, vol. 61, Issue 11, pp. 966-970, Abstract only (3 pages). (Year: 2006).

International Search Report and Written Opinion mailed Mar. 10, 2017, issued in corresponding International Application No. PCT/US2016/055809, filed Oct. 6, 2016, 11 pages.

Muizelaar, J.P., et al., "Improving the Outcome of Severe Head Injury With the Oxygen Radical Scavenger Polyethylene Glycol-Conjugated Superoxide Dismutase: A Phase II Trial," Journal of Neurosurgery 78(3):375-382, Mar. 1993.

•Non-Final Office Action mailed Jun. 30, 2020, issued in prior U.S. Appl. No. 15/766,314, filed Apr. 5, 2018, now U.S. Pat. No. 11,065,272, 7 pages.

•Final Office Action mailed Dec. 1, 2020, issued in prior U.S. Appl. No. 15/766,314, filed Apr. 5, 2018, now U.S. Pat. No. 11,065,272, 10 pages.

•International Preliminary Report on Patentability mailed Apr. 10, 2018, issued in corresponding International Application No. PCT/US2016/055809, filed Oct. 6, 2016, 8 pages.

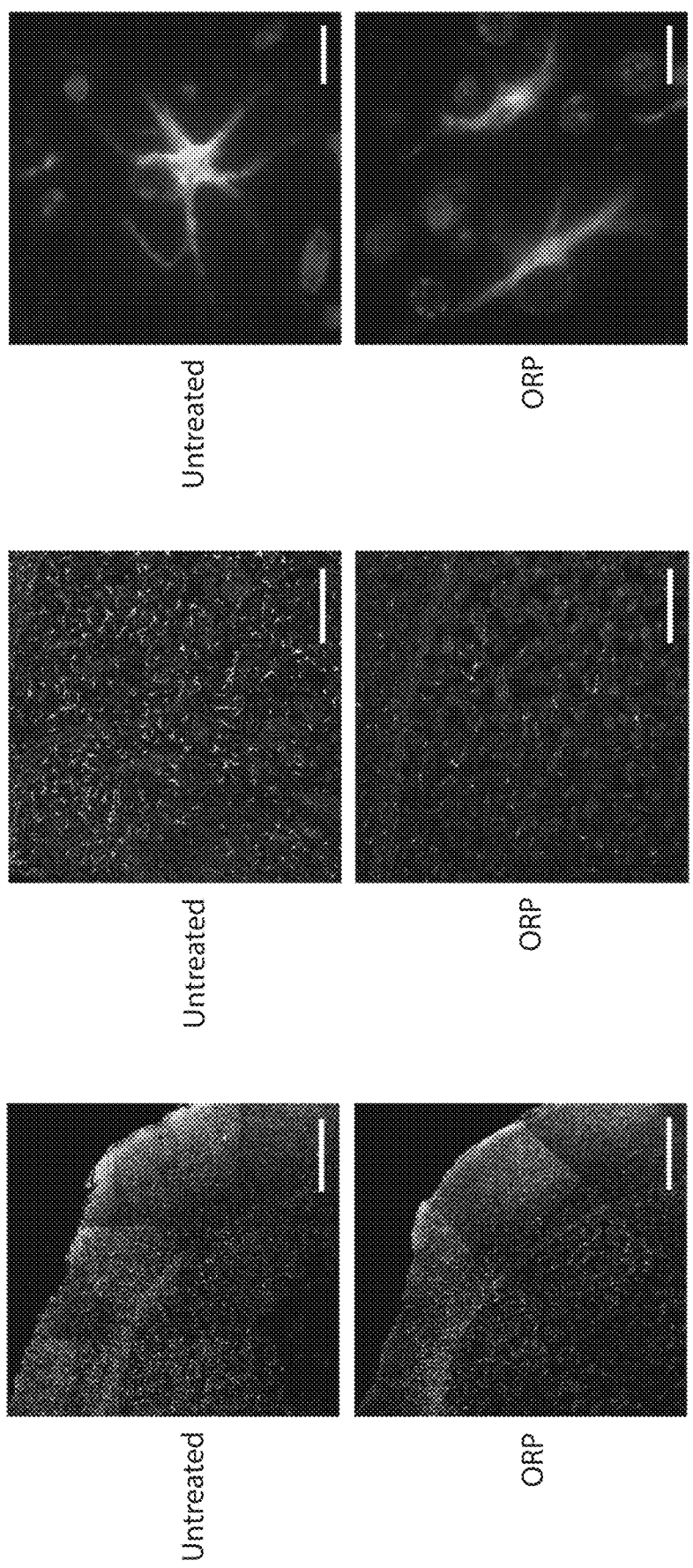

OXYGEN REACTIVE POLYMERS FOR TREATMENT OF TRAUMATIC BRAIN INJURY

CROSS-REFERENCES TO RELATED APPLICATIONS

This application is a continuation of U.S. application Ser. No. 15/766,314, filed Apr. 5, 2018, now U.S. Pat. No. 11,065,272, which is the national stage of International Application No. PCT/US2016/055809, filed Oct. 6, 2016, which claims the benefit of U.S. Patent Application No. 62/237,915, filed Oct. 6, 2015, each expressly incorporated herein by reference in its entirety.

BACKGROUND OF THE INVENTION

Traumatic brain injury (TBI) is a serious medical condition that may occur after the brain sustains a significant impact via linear or rotational forces. TBI is the leading cause of disability and death in people under 45 with approximately 10 million new cases each year worldwide. The effects of TBI can be severe, including severe neurocognitive, physical, and psychosocial impairment. Only incremental improvements in treatment have been made over the past century, and there remains a significant unmet need to develop strategies to avoid long-term damage from TBI.

The primary phase of TBI describes immediate neuronal damage from contusions or oxygen deprivation caused by global mass effect. Secondary injury occurs later via such mechanisms as reperfusion injury, delayed cortical edema, blood-brain barrier (BBB) breakdown, and local electrolyte imbalance. These disturbances themselves result in reactive oxygen species (ROS)-mediated neurodegeneration through calcium release, glutamate toxicity, lipid peroxidation, and mitochondrial dysfunction. Such secondary injury may occur in brain adjacent to the site of initial supposed injury, yielding the potential for unexpected spread of the zone of damage over months post-injury.

With the goal of treating secondary brain injury, ROS scavengers have become an increasingly popular potential treatment option. The compounds poly(ethylene glycol)-conjugated superoxide dismutase (PEG-SOD) and tirilizad have been considered for use in free-radical scavenging, but both antioxidant formulations did not show positive results in improving patient outcome after TBI, likely because of poor delivery into brain.

Preclinical studies suggest progesterone has neuroprotective effects in brain injury models likely by modulating native antioxidant activity levels. However, other central nervous system injuries treated with progesterone have not shown any improvement, and Phase III clinical trials have shown limited success. Cyclosporine A is being testing for its neuroprotective properties following TBI in an ongoing phase II study (NeuroSTAT) because of its ability to stabilize mitochondrial function. Cyclosporin A is thought to decrease excitotoxic and oxidative stress that occurs in secondary damage by stabilizing mitochondrial function in neurons. Indeed, cyclosporine A, administered post-TBI, has been shown to improve synaptic plasticity in rat models. In pre-clinical studies, carbon nanoparticles have been shown to act as an antioxidant to aid in elimination of radical species using rat models of TBI. Similarly, transcranial administration of the ROS scavenger, glutathione, has been shown to reduce secondary injury in a mouse model of TBI. Although significant progress has been made in understanding the complex pathophysiological response to TBI, reducing the damage associated with the reactive oxygen species (ROS)-dependent secondary phase of the injury remains a substantial challenge.

SUMMARY OF THE INVENTION

The present invention provides methods and compositions for treating traumatic brain injury.

In one aspect, the invention provides a method for treating traumatic brain injury. In one embodiment of the method, a therapeutically effective amount of an oxygen reactive polymer is administered to a subject in need thereof. In certain embodiments, treating traumatic brain injury comprises reducing neurodegeneration. In certain embodiments, treating traumatic brain injury comprises altering gliosis. In certain embodiments, gliosis is advantageously reduced. In other embodiments, gliosis is advantageously increased. In certain embodiments, treating traumatic brain injury comprises treating the secondary effects of traumatic brain injury. Representative secondary effects (or secondary injury) that are advantageously treated include one or more of reperfusion injury, delayed cortical edema, blood-brain barrier breakdown, local electrolyte imbalance, neurovascular unit dysfunction, and intracranial pressure. In certain embodiments, administering the polymer comprises intravenous, intranasal, intrathecal/intraventrical, or intracranial administration.

The oxygen reactive polymer can take the form of a nanoparticle. In certain of these embodiments, the nanoparticle comprises a single oxygen reactive polymer.

In the methods of the invention, the polymer comprises a reactive oxygen species scavenger group. Suitable reactive oxygen species scavenger groups include antioxidant groups. Representative reactive oxygen species scavenger groups include sulfur-containing groups in which the sulfur atom is oxidizable. In certain embodiments, the reactive oxygen species scavenger group is selected from the group consisting of a thioether, a thioketal, a thiol, a sulfide, a disulfide, a sulfoxide, and a sulfonate.

In certain embodiments, the polymer comprises a polyoxyalkylene oxide group (e.g., a polyoxyethylene oxide group).

In certain embodiments, the polymer further comprises a diagnostic group.

In another aspect, the invention provides oxygen reactive polymers. In certain embodiments, the invention provides therapeutic oxygen reactive copolymers (e.g., copolymers of formulae (I)-(III)). In other embodiments, the invention provides theranostic oxygen reactive copolymers (e.g., copolymers of formulae (IV)-(VI)).

In one embodiment, the invention provides a copolymer comprising
(a) an oxygen scavenger-containing repeating unit, and
(b) a polyalkylene oxide-containing repeating unit,
wherein the copolymer has formula (I)

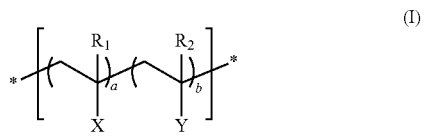

wherein

X is a first pendant group comprising an oxygen scavenger group,
Y is a second pendant group comprising a polyalklyene oxide group,
$R_1$ and $R_2$ are independently selected from hydrogen or methyl,
a is the mole fraction of the oxygen scavenger-containing repeating unit and is from about 0.25 to about 0.95 (25-95 mol %),
b is the mole fraction of the polyalkylene oxide-containing repeating unit and is from about 0.05 to about 0.75 (5-75 mol %),
a+b is 1.0, and
\* represents the remainder of the copolymer.

In certain of these embodiments, the copolymer has formula (II)

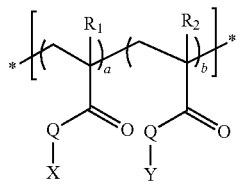

(II)

wherein Q at each occurrence is independently selected from O or N.

In other of these embodiments, the copolymer has formula (III)

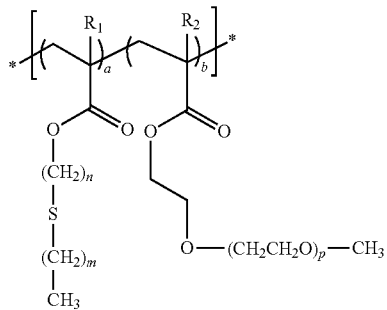

(III)

wherein
n is an integer from 1 to 12,
m is an integer from 0 to 12, and
p is an integer from 6 to 40.

In another embodiment, the invention provides a copolymer comprising
(a) an oxygen scavenger-containing repeating unit,
(b) a polyalkylene oxide-containing repeating unit, and
(c) a diagnostic group-containing repeating unit,
wherein the copolymer has formula (IV)

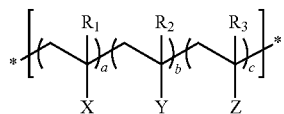

(IV)

wherein
X is a first pendant group comprising an oxygen scavenger group,
Y is a second pendant group comprising a polyalklyene oxide group,
$R_1$, $R_2$, and $R_3$ are independently selected from hydrogen or methyl,
Z is a third pendant group comprising a diagnostic group,
a is the mole fraction of the oxygen scavenger-containing repeating unit and is from about 0.25 to about 0.95 (25-95 mol %),
b is the mole fraction of the polyalkylene oxide-containing repeating unit and is from about 0.05 to about 0.75 (5-75 mol %),
c is the mole fraction of the diagnostic group-containing repeating unit and is from about 0.005 to about 0.10 (0.5-10 mol %),
a+b+c is 1.0; and
\* represents the remainder of the copolymer.

In certain of these embodiments, the copolymer has formula (V)

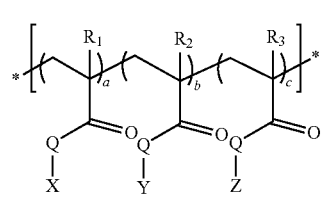

(V)

wherein Q at each occurrence is independently selected from O or N.

In other of these embodiments, the copolymer has formula (VI)

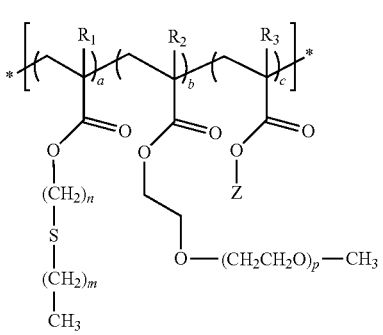

(VI)

wherein
n is an integer from 1 to 12,
m is an integer from 0 to 12, and
p is an integer from 6 to 40.

In certain embodiments, the polymer is a random copolymer.

The copolymers of formulae (I)-(VI) are oxygen reactive polymers useful in the methods of the invention.

In a further aspect, the invention provides pharmaceutical compositions that an oxygen reactive polymer, such as a copolymer of formulae (I)-(VI).

In another aspect, the invention provides a nanoparticle, comprising an oxygen reactive polymer, such as a copolymer of formulae (I)-(VI). In certain embodiments, the nanoparticle comprises a single copolymer.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 1A shows the preparation of a representative theranostic oxygen reactive polymer (ORP) of the invention. FIG. 1B shows the $^1$H NMR analysis of the representative ORP (carboxylic acid pre-diagnostic group coupling) with identified peaks. FIG. 1C shows the gel permeation chromatography (GPC) elution profile indicating monodispersity of the final representative ORP (with gadolinium diagnostic group). FIG. 1D shows the inductively-coupled plasma (ICP) analysis of gadolinium (Gd) content in the representative ORP. Data is from three separate batches of the ORP. FIG. 1E shows a schematic illustration of reaction of the representative ORP with reactive oxygen species (ROS) and a DCFH-DA assay showing the reduction in $H_2O_2$-induced conversion of non-fluorescent DCFH to highly fluorescent DCF in the presence of the representative ORP (ORP) compare to untreated (UT). FIG. 1F compares images showing DCFH-DA fluorescence in human astrocytes exposed to 1 mM $H_2O_2$ in the presence (ORP) or absence of ORP (UT). Light spots (green fluorescence) of DCFH indicate the presence of ROS in cells from brightfield (BF) images. Scale bar represents 250 μm.

FIG. 2A compares T1-weighted MR images (TE=4.5 ms, TR=667.5 ms) showing accumulation of the ORP throughout the damaged region. Accumulation of the ORP was observed throughout the damaged region of brain as early as 3 hrs after injection as indicated by the elevated T1 signals in damaged brain (white arrows). Enhancement in T1 is observed throughout the damage after 24 hrs indicating the retention of ORP within damaged brain. FIG. 2B compares T2 RARE (TE=90 ms, TR=3000 ms) MR images showing the edema caused by TBI and provides an indication of the extent of damage (white arrows). T1 RARE (TE=10 ms, TR=500 ms) images show the accumulation of ORP seen as higher signal intensity regions correlates with damaged regions observed from T2 RARE images. FIG. 2C compares T1 signal intensity as a function of time and shows uptake and retention of the representative ORP within damaged brain whereas it is cleared from other regions. Time 0 represents the T1 signal prior to injection of the ORP.

FIGS. 4A-4E illustrate that a representative ORP reduced astrogliosis in CCI mouse models of TBI. ORP treatment reduced reactive astrocytes surrounding damage seen 7 days after TBI. FIG. 4A compares composite images of GFAP staining in mouse brains indicating reactive astrocytes were present well below the initial damage in brains from untreated mice (Untreated), and were minimally present below damage in brains from ORP-treated mice (ORP). Scale bar represents 500 μm. FIG. 4B compares low powered field of GFAP staining in mouse brains from FIG. 4A showing greater detail of the higher density of reactive astrocytes in brains from untreated mice. Scale bar represents 200 μm. FIG. 4C compares high resolution images of GFAP staining showing a typical reactive astrocyte present in the brains of the untreated mice (Untreated) and minimally reactive astrocyte in the brains of the ORP-treated mice (ORP). Scale bar represents 10 μm. FIG. 4D compares manual counts of GFAP-positive cells below the damaged region of brain quantitatively showing the lower number of reactive astrocytes in the brains of ORP-treated mice. FIG. 4E compares manual counts of the numbers of processes per GFAP-positive cells indicating the astrocytes in the brains of ORP-treated mice were much less reactive.

FIG. 5A compares low powered images of Iba1 staining in mouse brains indicating activated microglia were present well below the initial damage in brains from untreated mice (UT), and were minimally present below damage in brains from ORP-treated mice (ORP). This further suggests the ORP is able to suppress secondary damage caused by release of ROS into surrounding brain. Scale bar represents 50 μm. FIG. 5B compares high powered field of Iba1 staining in mouse brains showing higher density and activation of microglia in brains from untreated mice. Scale bar represents 20 μm. FIG. 5C compares manual counts of Iba1-positive cells adjacent to the cortical injury quantitatively showing the lower number of microglia in ORP-treated mice. FIG. 5D compares pixel density (positive pixels per $μm^2$) of Iba1 immunostaining at 200× magnification indicating the higher activation of microglia in untreated animals.

FIG. 6A compares T1-weighted (TE=4.5 ms, TR=667.5 ms) images of contrast enhancement from ORP in CCI-damaged brain. FIG. 6B is a T2-weighted image showing edema caused by TBI. FIG. 6C shows the quantification of change in signal intensity before and after ORP injection in TBI mice and reveals that ORP accumulates and is retained in the damaged brain. FIG. 6D compares T1-weighted images of animals injected with Magnevist (Gd-DTPA). FIG. 6E is a T2-weighted image showing edema caused by TBI. FIG. 6F compares intravascular signal change as a function of time and indicates the representative ORP has a circulation half-life of about 1.1 hrs whereas Gd-DTPA has a 36 min blood half-life. FIG. 6G compares the change in signal intensity in the damaged region of brain as a function of time and indicates the resident half-life of Gd-DTPA is approximately 4 hrs and the representative ORP is greater than 14 hrs.

DETAILED DESCRIPTION OF THE INVENTION

The present invention provides methods and compositions for treating traumatic brain injury. The methods and compositions utilize a multi-functional oxygen reactive polymer (ORP) that includes repeating units that include a reactive oxygen species (ROS) scavenging group and a polyalkylene oxide group. For theranostic applications, the oxygen reactive polymer further includes a diagnostic group.

Methods for Treating Traumatic Brain Injury

In one aspect, the invention provides a method for treating traumatic brain injury. In one embodiment of the method, a therapeutically effective amount of an oxygen reactive polymer is administered to a subject in need thereof.

In certain embodiments, treating traumatic brain injury comprises reducing neurodegeneration. As described further below, a 10-fold reduction was observed in a mouse model.

In certain embodiments, treating traumatic brain injury comprises altering gliosis. In certain embodiments, gliosis is advantageously reduced. In other embodiments, gliosis is advantageously increased. As described further below, a 2-fold reduction was observed in a mouse model.

In certain embodiments, treating traumatic brain injury comprises treating the secondary effects of traumatic brain injury. Representative secondary effects (or secondary injury) that are advantageously treated include one or more of reperfusion injury, delayed cortical edema, blood-brain barrier breakdown, local electrolyte imbalance, neurovascular unit dysfunction, and intracranial pressure.

In certain embodiments, administering the polymer comprises intravenous, intranasal, intrathecal/intraventrical, or intracranial administration.

The oxygen reactive polymer can take the form of a nanoparticle. In certain of these embodiments, the nanoparticle comprises a single oxygen reactive polymer.

Figure 1A:
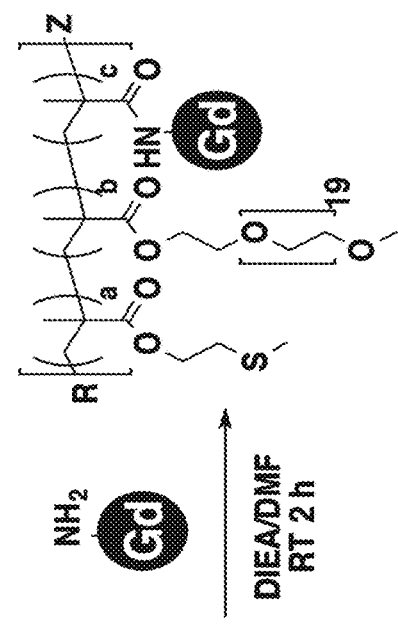
FIGS. 1A-1F show the preparation and characterization of a representative oxygen reactive polymer (ORP) nanoparticle of the invention.
Figure 1A:
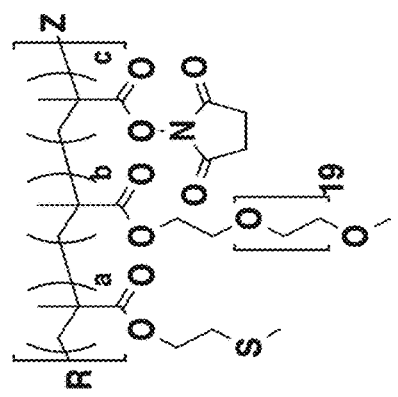
Figure 1A:
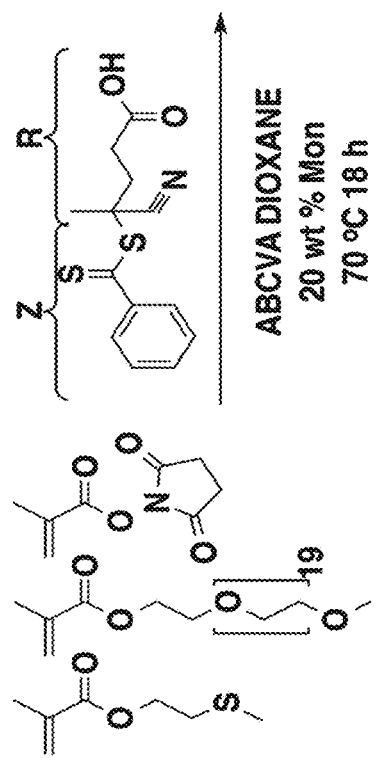

As shown in FIG. 1A, the oxygen reactive polymer is a copolymer. In certain embodiments, copolymer is a random copolymer. In certain embodiments, copolymer is a not a block copolymer.

To facilitate reactive oxygen species neutralization, the polymer includes repeating units that include a reactive oxygen species scavenger group. Suitable reactive oxygen species scavenger groups include groups that are antioxidants (e.g., vitamin C moieties or phenolic moieties). In certain embodiments, reactive oxygen species scavenger groups are sulfur-containing groups. Representative reactive oxygen species scavenger groups include thioether, thioketal, thiol (sulfhydryl), sulfide, disulfide, sulfoxide, and sulfonate groups.

In certain embodiments, the reactive oxygen species scavenger group is a thioether having the formula $-(CH_2)_n-S-(CH_2)_m-$, where n is an integer from 1 to 12 and m is an integer from 0 to 12. In general, smaller alkyl segments allow for a higher molar incorporation of the oxygen reactive groups to be present at a given injection concentration. In certain embodiments, n is 2 and m is 0 or 1. In one embodiment, the thioether has the formula $-(CH_2)_n-S-(CH_2)_mCH_3$, where n=2 and m=0 (i.e., $-CH_2CH_2-S-CH_3$).

To impart advantageous circulatory system and stability properties, the polymer includes repeating units that include a polyoxyalkylene oxide group. In certain embodiments, the polyoxyalkylene oxide group is a polyoxyethylene oxide group. In certain embodiments, the polyoxyalkylene oxide group has the formula $-(OCH_2CH_2)_p-$, where p is an integer from 6 to 40. Suitable polyoxyalkylene oxide groups are described below.

For theranostic applications, the polymer includes repeating units that include a diagnostic group. Suitable diagnostic groups include any group that can be associated with the polymer and provide a signal indicating the presence and location of the polymer in the subject to which the polymer has been administered or tissue contacted with the polymer. Representative diagnostic groups include magnetic resonance imaging groups, radiolabel groups, fluorescent groups, luminescent groups, X-ray/CT groups, and ultrasound groups. Suitable diagnostic groups are described below.

In certain embodiments, the polymer further includes a targeting agent for directing the polymer to the target tissue. In certain embodiments, the targeting agent is an agent that binds to the cell surface of the target tissue. Suitable targeting agents include small molecules (e.g. vitamins), peptides, and proteins.

Imaging Methods

In another aspects, the invention provides methods for using oxygen reactive polymers as described herein to image tissues (i.e., in vivo and in vitro). The methods include imaging methods such as magnetic resonance imaging when the polymer has magnetic resonance activity (i.e., diagnostic group is an MRI active group), and optical imaging when the polymer includes an optical diagnostic group (e.g., luminescent or fluorescent group).

In one embodiment, the invention provides a method for detecting (or imaging) cells or tissues by magnetic resonance imaging. In the method, the presence of the polymer is measured by magnetic resonance imaging techniques. In another embodiment, the invention provides a method for detecting (or imaging) cells or tissues by optical imaging. In the method, the presence of the polymer is measured by optical imaging techniques, such as measuring fluorescent or luminescence. The methods are applicable to detecting or imaging cells or tissues in vitro and in vivo.

Oxygen Reactive Polymers

In another aspect, the invention provides oxygen reactive polymers. In certain embodiments, the invention provides therapeutic oxygen reactive copolymers (e.g., copolymers of formulae (I)-(III)). Therapeutic oxygen reactive copolymers include reactive oxygen species scavenger-containing repeating units. In other embodiments, the invention provides theranostic oxygen reactive copolymers (e.g., copolymers of formulae (IV)-(VI)). Theranostic oxygen reactive copolymers include one or more oxygen scavenger-containing repeating units and one or more diagnostic group-containing repeating units. The polymers are useful in the methods of the invention.

In one embodiment, the invention provides a copolymer comprising
(a) an oxygen scavenger-containing repeating unit, and
(b) a polyalkylene oxide-containing repeating unit,
wherein the copolymer has formula (I)

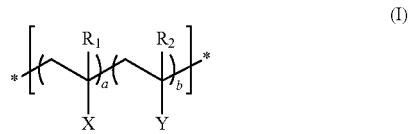

(I)

wherein
X is a first pendant group comprising an oxygen scavenger group,
Y is a second pendant group comprising a polyalklyene oxide group,
$R_1$ and $R_2$ are independently selected from hydrogen or methyl,
a is the mole fraction of the oxygen scavenger-containing repeating unit and is from about 0.25 to about 0.95 (25-95 mol %), b is the mole fraction of the polyalkylene oxide-containing repeating unit and is from about 0.05 to about 0.75 (5-75 mol %), a+b is 1.0, and \* represents the remainder of the copolymer.

In certain embodiments of formula (I), b is from about 0.05 to about 0.50 (5-50 mol %).

In certain of these embodiments, the copolymer has formula (II)

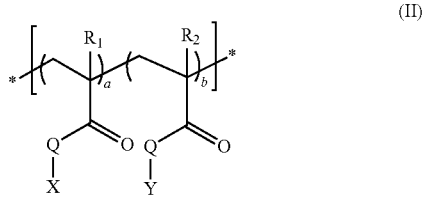

(II)

wherein Q at each occurrence is independently selected from O or N.

In other of these embodiments, the copolymer has formula (III)

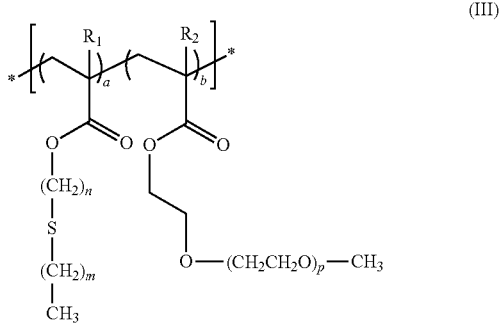

(III)

wherein n is an integer from 1 to 12, m is an integer from 0 to 12, and p is an integer from 6 to 40.

In certain of these embodiments, n is from 1 to 5 (e.g., 2), and m is 0-2 (e.g., 0).

In another embodiment, the invention provides a copolymer comprising (a) an oxygen scavenger-containing repeating unit, (b) a polyalkylene oxide-containing repeating unit, and (c) a diagnostic group-containing repeating unit, wherein the copolymer has formula (IV)

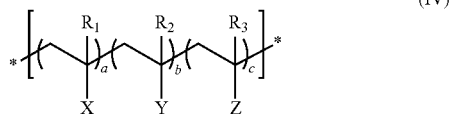

(IV)

wherein

X is a first pendant group comprising an oxygen scavenger group,

Y is a second pendant group comprising a polyalklyene oxide group, $R_1$, $R_2$, and $R_3$ are independently selected from hydrogen or methyl, Z is a third pendant group comprising a diagnostic group, a is the mole fraction of the oxygen scavenger-containing repeating unit and is from about 0.25 to about 0.95 (25-95 mol %), b is the mole fraction of the polyalkylene oxide-containing repeating unit and is from about 0.05 to about 0.75 (5-75 mol %), c is the mole fraction of the diagnostic group-containing repeating unit and is from about 0.005 to about 0.10 (0.5-10 mol %), a+b+c is 1.0; and \* represents the remainder of the copolymer.

In certain embodiments of formula (IV), b is from about 0.05 to about 0.50 (5-50 mol %).

In certain of these embodiments, the copolymer has formula (V)

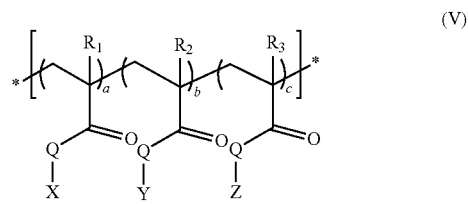

(V)

wherein Q at each occurrence is independently selected from O or N.

In other of these embodiments, the copolymer has formula (VI)

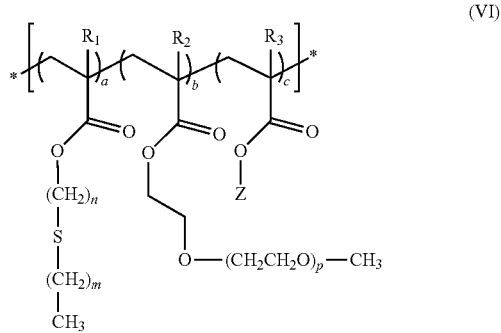

(VI)

wherein n is an integer from 1 to 12, m is an integer from 0 to 12, and p is an integer from 6 to 40.

The following is a description of features of the copolymers of formulae (I)-(VI).

As noted above, to facilitate reactive oxygen species neutralization, the polymer includes repeating units that include a reactive oxygen species scavenger group. As used herein, the terms "oxygen scavenger group" and "oxygen scavenger-containing repeating unit" refer to chemical groups (i.e., groups of atoms) that react with an remove reactive oxygen species, and repeating units of the polymer that include these groups (e.g., monomers that include oxygen scavenger groups that are copolymerized with other monomers to provide the copolymers). Suitable reactive oxygen species scavenger groups include sulfur-containing groups. Representative reactive oxygen species scavenger groups include thioether, thioketal, thiol (sulfhydryl), sulfide, disulfide, sulfoxide, and sulfonate groups. In certain embodiments, the reactive oxygen species scavenger group is a thioether having the formula —$(CH_2)_n$—S—$(CH_2)_m$—, where n is an integer from 1 to 12 and m is an integer from 0 to 12. In one embodiment, the thioether has the formula —$(CH_2)_n$—S—$(CH_2)_m CH_3$, where n=2 and m=0.

As noted above, to impart advantageous circulatory system and stability properties, the polymer includes repeating units that include a polyoxyalkylene oxide group. As used herein, the terms "polyoxyalkylene oxide group" and "polyoxyalkylene oxide-containing repeating unit" refer to chemical groups (i.e., groups of atoms) that include a polyoxyalkylene oxide group, and repeating units of the polymer that include these groups (e.g., monomers that include polyoxyalkylene oxide groups that are copolymerized with other monomers to provide the copolymers). In certain embodiments, the polyoxyalkylene oxide group is a polyoxyethylene oxide group. In certain embodiments, the polyoxyalkylene oxide group has the formula —$(OCH_2CH_2)_p$—, where p is an integer from 6 to 40. Suitable poly(ethylene oxide) groups include poly(ethylene oxides) (PEO or PEG) and poly(ethylene oxide) copolymers such as block copolymers that include poly(ethylene oxide) and poly(propylene oxide) (e.g., PEO-PPO and PEO-PPO-PEO). In one embodiment, the poly(ethylene oxide) group is a poly(ethylene oxide). In certain embodiments, poly(ethylene oxide) group has a molecular weight (weight average, Mw) of from about 0.3 to about 5 kDa. In others embodiments, the poly(ethylene oxide) group has a molecular weight of from about 0.3 to about 2 kDa. In certain embodiments, polyoxyalkylene oxide-containing polymers of the invention are prepared from commercially available polyoxyalkylene oxide-containing monomers (e.g., PEGMAs) having molecular weights of 300, 950, and 2000 g/mole.

As noted above, for theranostic applications, the polymer includes repeating units that include a diagnostic group. As used herein, the terms "diagnostic group" and "diagnostic group-containing repeating unit" refer to chemical groups (i.e., groups of atoms) that provide a detectable signal indicating the presence and location of the polymer in the subject to which the polymer has been administered or tissue contacted with the polymer. These polymers may be prepared from monomers that include diagnostic groups that are copolymerized with other monomers to provide the copolymers, or monomers bearing reactive groups that may be modified post-polymer formation to provide a polymer that includes the diagnostic group). Representative diagnostic groups include magnetic resonance imaging groups, radiolabel groups, fluorescent groups, luminescent groups, X-ray/CT groups, and ultrasound groups. Suitable diagnostic groups include optical agents, such as fluorescent agents that emit light in the visible and near-infrared (e.g., fluorescein and cyanine derivatives). Suitable fluorescent agents include fluorescein and derivatives, rhodamine and derivatives, and cyanines. Representative fluorescent agents include fluorescein, OREGON GREEN 488, ALEXA FLUOR 555, ALEXA FLUOR 647, ALEXA FLUOR 680, Cy5, Cy5.5, and Cy7.

As noted above, in certain embodiments, the polymer further includes a targeting agent for directing the polymer to the target tissue. In certain embodiments, the targeting agent is an agent that binds to the cell surface of the target tissue. Suitable targeting agents include small molecules (e.g. vitamins), peptides, and proteins.

As used herein, the term "pendant group" comprising an oxygen scavenging group, a polyalkylene oxide group, or a diagnostic group refers to a group of atoms that is pendant from the polymer backbone (e.g., polyacrylate or polymethacrylate backbone) that includes an oxygen scavenging group, a polyalkylene oxide group, or a diagnostic group, respectively. The nature of the pendant group may vary and need not be the same for each of the oxygen scavenging group, polyalkylene oxide group, and diagnostic group. In certain embodiments, the pendant group (X, Y, and Z) includes an amide (Q is N) or ester (Q is O) group that covalently couples the oxygen scavenging group, polyalkylene oxide group, and diagnostic group to the polymer backbone. See, for example, formulae (II) and (IV). For biocompatibility and biodegradation purpose, in certain embodiment, Q is O and the linkage to the polymer backbone is an ester, which is readily degraded to provide a minimal backbone segment.

Referring to copolymer formulae (I)-(V), each copolymer is shown as having repeating units and the remainder of the copolymer is indicated as * at the polymer termini. The "remainder of the copolymer" may vary depending on the method by which the copolymer is made. For example, when the copolymer is made by RAFT polymerization processes, the copolymer termini are determined by the RAFT agent (e.g., a thiocarbonylthio compound having formula Z—C(=S)—S—R). In these embodiments, the product polymer has the R group at one end and a dithiocarbonate moiety, Z—C(=S)—S—, at the other end. Referring to FIG. 1A, exemplary raft agent Ph-C(=S)—S—C$(CH_3)(CN)CH_2CH_2CO_2H$, where Z is Ph (phenyl) and R is C$(CH_3)(CN)CH_2CH_2CO_2H$, provides a copolymer having R as the remainder of the copolymer at one terminus and having Z as the remainder of the copolymer at the other terminus.

As shown in FIG. 1A, the oxygen reactive polymer is a copolymer. In certain embodiments, copolymer is a random copolymer. In certain embodiments, copolymer is a not a block copolymer.

The copolymers of the invention can take the form of a nanoparticle. In certain of these embodiments, the nanoparticle comprises a single copolymer. Suitable particles have a hydrodynamic size less than about 200 nm. In certain embodiments, the nanoparticles have a hydrodynamic size from about 4 to about 100 nm. In certain embodiments, the nanoparticles have a hydrodynamic size of about 100 nm. In other embodiments, the nanoparticles have a hydrodynamic size of about 25 nm. As used herein, the term "hydrodynamic size" refers the radius of a hard sphere that diffuses at the same rate as the particle under examination as measured by DLS. The hydrodynamic radius is calculated using the particle diffusion coefficient and the Stokes-Einstein equation given below, where k is the Boltzmann constant, T is the temperature, and η is the dispersant viscosity: $R_H = kT/6\pi\eta D$.

A single exponential or Cumulant fit of the correlation curve is the fitting procedure recommended by the International Standards Organization (ISO). The hydrodynamic size extracted using this method is an intensity weighted average called the Z average.

To take advantage of the EPR retention effect, in certain embodiments, the polymer has a hydrodynamic diameter from about 4 to about 100 nm.

In certain embodiments, the polymer has a molar mass dispersity (Đ) that ranges is from about 1 to about 2. In certain embodiments, the polymer has a molar mass dispersity values between about 1.05 and about 1.30. In certain embodiments the polymer has a molar mass dispersity of about 1.20.

In certain embodiments, the polymer has a number average molecular weight ($M_n$) from about 5,000 to about 100,000 (i.e., 5-100 kDa).

Pharmaceutical Compositions and Administration

In another aspect of the invention, a composition is provided that includes an oxygen reactive polymer (e.g., nanoparticle) of the invention and a carrier suitable for administration to a warm-blooded subject (e.g., a human subject). Suitable carriers include those suitable for intravenous injection (e.g., saline or dextrose) and nasal delivery.

Pharmaceutical compositions of the invention include an effective amount of oxygen reactive polymer dispersed in a pharmaceutically acceptable carrier. As used herein, the term "effective" (e.g., "an effective amount") means adequate to accomplish a desired, expected, or intended result. The phrases "pharmaceutically acceptable" refers to molecular entities and compositions that do not produce an adverse, allergic, or other untoward reaction when administered to an animal, such as, for example, a human, as appropriate.

Guidelines for the preparation of a pharmaceutical composition that contains at least one additional active ingredient, such as a pharmaceutically acceptable carrier, may be provided in light of the present disclosure and through consultation of *Remington's Pharmaceutical Sciences,* 18th Ed. Mack Printing Company, 1990. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials, and combinations thereof as would be known to one of ordinary skill in the art (see, for example, Remington's Pharmaceutical Sciences, pp 1289-1329, 1990).

The oxygen reactive polymers of the invention may be administered intravenously, intranasally, intrathecally/intraventricaly, or intracranially, such as during a surgery.

Pharmaceutical compositions comprising the oxygen reactive polymers may be adapted for administration via any method known to those of skill in the art, such as the methods described above.

The actual dosage amount of a nanoparticle as described herein administered to a subject may be determined by physical and physiological factors such as body weight, severity of condition, the type of disease being detected, or monitored, previous or concurrent therapeutic interventions, idiopathy of the patient, and on the route of administration. The practitioner responsible for administration will typically determine the concentration of active ingredient(s) in a composition and appropriate dose(s) for the individual subject. Nanoparticles of the present invention may be cleared by the kidneys; thus, it may be important to assess any underlying problems with kidney function. Kidney function may be assessed by measuring the blood levels of creatinine, a protein normally found in the body. If these levels are higher than normal, it is an indication that the kidneys may not be functioning at an optimal rate and dosage may be lowered accordingly.

The dose may be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 5-30 minutes, about 0.5-1 hour, about 1-2 hours, about 2-6 hours, about 6-10 hours, about 10-24 hours, about 1-2 days, about 1-2 weeks, or longer, or any time interval derivable within any of these recited ranges.

In certain embodiments, pharmaceutical compositions comprise, for example, at least about 0.1% of a polymer as described herein. In other embodiments, a polymer comprises between about 2% to about 75% of the weight of the unit, or between about 25% to about 60%, for example, and any range derivable therein. In other non-limiting examples, a dose comprises from about, at most about, or at least about 1, 5, 10, 50, or 100 microgram/kg/body weight, 1, 5, 10, 50, or 100 milligram/kg/body weight, or 1000 mg/kg/body weight or more per administration, or any range derivable therein. In non-limiting examples of a derivable range from the numbers listed herein, a range of about 5 mg/kg/body weight to about 100 mg/kg/body weight or about 5 microgram/kg/body weight to about 500 milligram/kg/body weight can be administered.

Sterile injectable formulations may be prepared by incorporating an oxygen reactive polymer in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, certain methods of preparation may include vacuum-drying or freeze-drying techniques that yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration delivering high concentrations of the active agents to a small area.

As used herein, the term "about" refers to +/−5% of the recited value. The following is a description of representative nanoparticles of the invention and methods for their use.

ORP Development and Physical Characterization

RAFT polymerization was used to synthesize ORPs, providing a versatile platform for controlled synthesis of polymers with high monodispersity and reproducibility. The representative ORP contains PEG for increased circulation half-life and biocompatibility, gadolinium for providing contrast in magnetic resonance imaging (MRI), and a thioether containing unit for ROS scavenging. By mass, the ORP primarily consists of PEG to maintain biocompatibility. By mole, the ORP is dominantly thioether to maximize the ROS sponge capacity.

Synthesis of the ORPs was accomplished via reversible addition-fragmentation chain transfer (RAFT) polymerization by copolymerizing polyethylene glycol methacrylate (PEGMA, Mn about 1000 Da) with a thioether containing monomer (MEM) and the amine reactive monomer MNHS (FIG. 1A). The dense poly(PEGMA) brush copolymer was designed to facilitate facile administration and biocompatibility at high ORP concentrations (injection concentrations of about 100 mg/mL). Recently conditions were developed that allow PEGMA with a molecular weight of about 1000 Da (about 19 EG repeats) to be polymerized with a high level of control (PDIs about 1.10). See, Roy, D.; Berguig, G. Y.; Ghosn, B.; Lane, D.; Braswell, S.; Stayton, P. S.; Convertine, A. J. Synthesis and characterization of transferrin-targeted chemotherapeutic delivery systems prepared via RAFT copolymerization of high molecular weight PEG macromonomers. *Polym Chem* 2014, 5, 1791-1799; and Lane, D. D.; Chiu, D. Y.; Su, F. Y.; Srinivasan, S.; Kern, H. B.; Press, O. W.; Stayton, P. S.; Convertine, A. J. Well-defined single polymer nanoparticles for the antibody-targeted delivery of chemotherapeutic agents. *Polym Chem* 2015, 6, 1286-1299. Work with poly(PEGMA)-based materials have shown no statistical change in enzyme levels even at polymer doses of 300 mg/kg. See, Berguig, G. Y.; Convertine, A. J.; Frayo, S.; Kern, H. B.; Procko, E.; Roy, D.; Srinivasan, S.; Margineantu, D. H.; Booth, G.; Palanca-Wessels, M. C.; Baker, D.; Hockenbery, D.; Press, O. W.; Stayton, P. S. Intracellular delivery system for antibody-Peptide drug conjugates. *Mol Ther* 2015, 23, 907-17.

A key advantage of this design is that it allows the ORP to achieve a high ethylene glycol weight percentage at relatively low degrees of polymerization (monomer numbers). This is important in regard to polymer clearance and biocompatibility, because all the monomers are designed with ester junctions at the carbon backbone to degrade down to the minimal backbone segment.

Figure 1C:
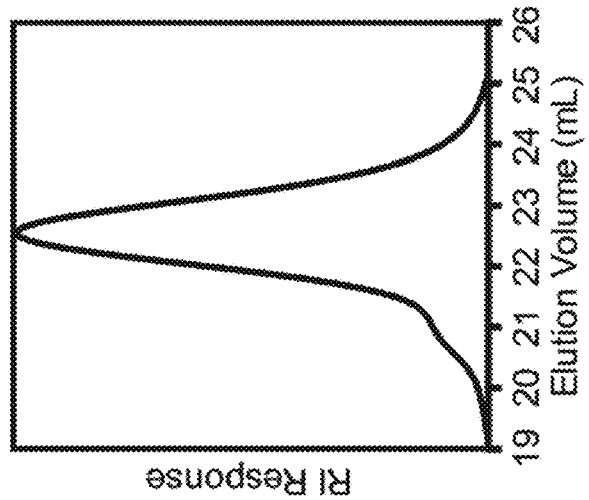
Figure 1B:
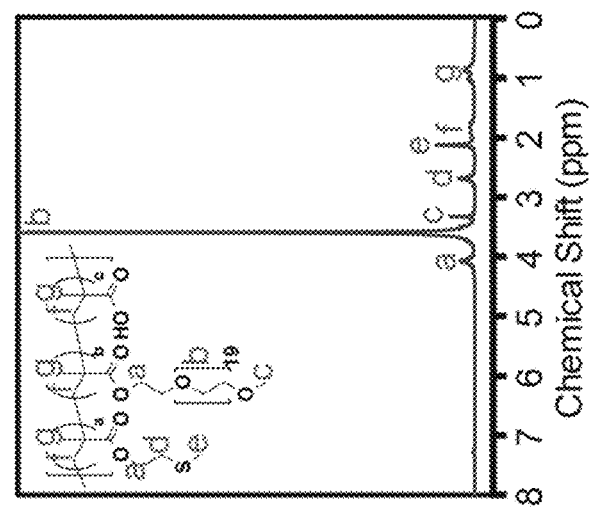
Figure 1F:
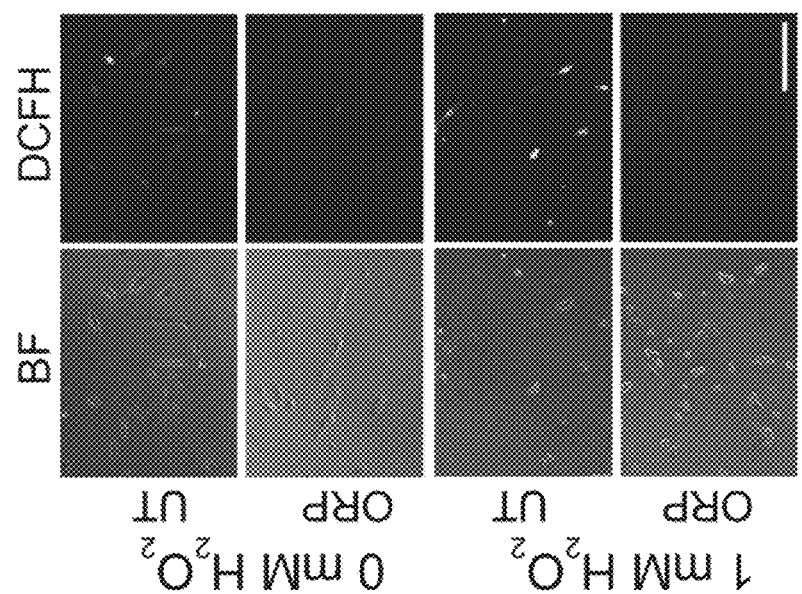

In order to maximize the accessibility of the reactive oxygen scavenging MEM residues within the aqueous phase, these groups were distributed randomly throughout the copolymer. This distribution prevents the hydrophobic moieties on the polymer chain from self-assembling into micelles or other macrostructures with diminished functionality. The composition, molecular weight, and molar mass dispersity (Đ) of the ORP were determined via a combination of $^1$H NMR spectroscopy and GPC (FIGS. 1B and 1C). Based on this treatment, the percentage of the MEM, O950, and MNHS co-monomers was determined to be 73, 21, and 6 mol % respectively, in good agreement with the feed values (i.e., 70, 25, and 5 mol %). The Gd contrast agent was then conjugated to the polymer via reaction of pendant N-hydroxysuccinimide ester groups with Gd-DO3A-Butylamine in DMSO. Following purification, the amount of conjugated Gd was quantified via inductively coupled plasma atomic emission spectroscopy (ICP-AES) to be 6.2±4.6 µg Gd/mg ORP (FIG. 1C) or approximately 3 Gd per 2 ORP. A summary of ORP properties is provided in Table 1.

TABLE 1

Physicochemical and structural properties of ORP.

| Molecular weight (g/mole) | Dispersity | Molar composition (mole %) | | Mass composition (wt %) | | Hydrodynamic size (nm) |
|---|---|---|---|---|---|---|
| 35,600 | 1.09 | MEM | 73 | MEM | 43 | 8 |
|  |  | O950 | 21 | O950 | 53 |  |
|  |  | MNHS | 6 | MNHS | 4 |  |
|  |  | Gd | 0.005 | Gd | 0.003 |  |

ROS Sponge Capacity of ORP

Figure 1E:
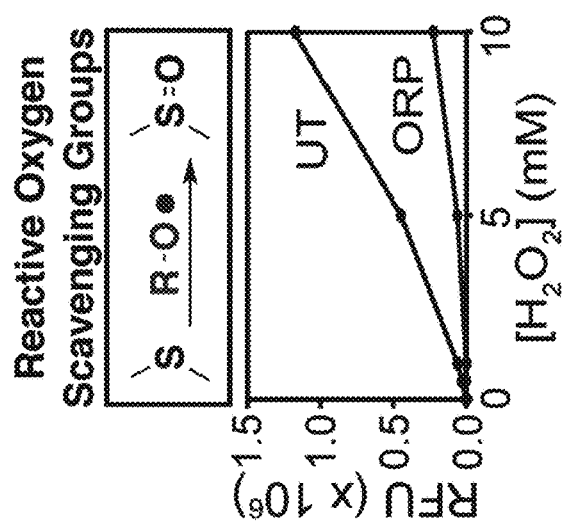
Figure 1D:
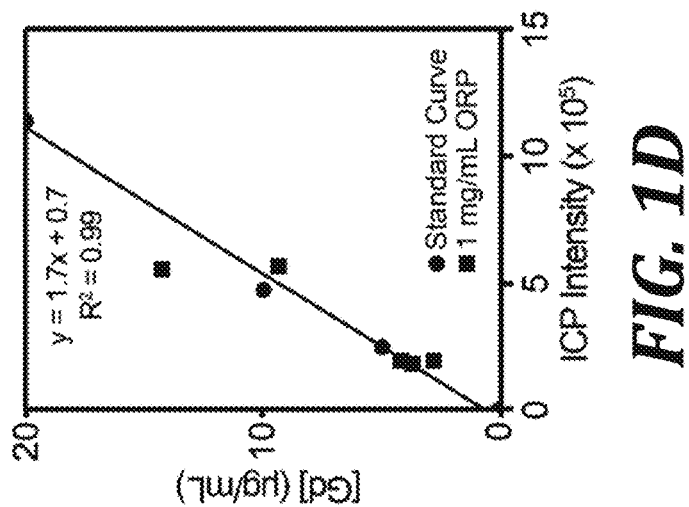

The 2,7-dichlorodihydrofluorescein diacetate (DCFH-DA) assay was used for fluorometric detection of ROS. Following the enzymatic or base-catalyzed cleavage of the diacetate group, DCFH is oxidized into the highly fluorescence DCF compound in the presence of ROS, which can be detected by fluorescence spectroscopy. The presence of ORP significantly reduced the levels of $H_2O_2$ and reduced the conversion of DCFH to DCF (FIG. 1D). At 10 mM $H_2O_2$ this corresponds to approximately 820 nmoles of ROS per mg of ORP, or 29 ROS per ORP. To test the effects of ORP and ROS reduction on astrocytes, which become activated in the presence of ROS, human astrocytes were exposed to $H_2O_2$ in the presence or absence of ORP. Staining the cells with DCFH revealed their intracellular ROS, which was significantly reduced when the cells were treated with ORP as evidenced by the lack of intracellular green fluorescence from DCF (FIG. 1E).

ORP Accumulates in TBI

Figure 2A:
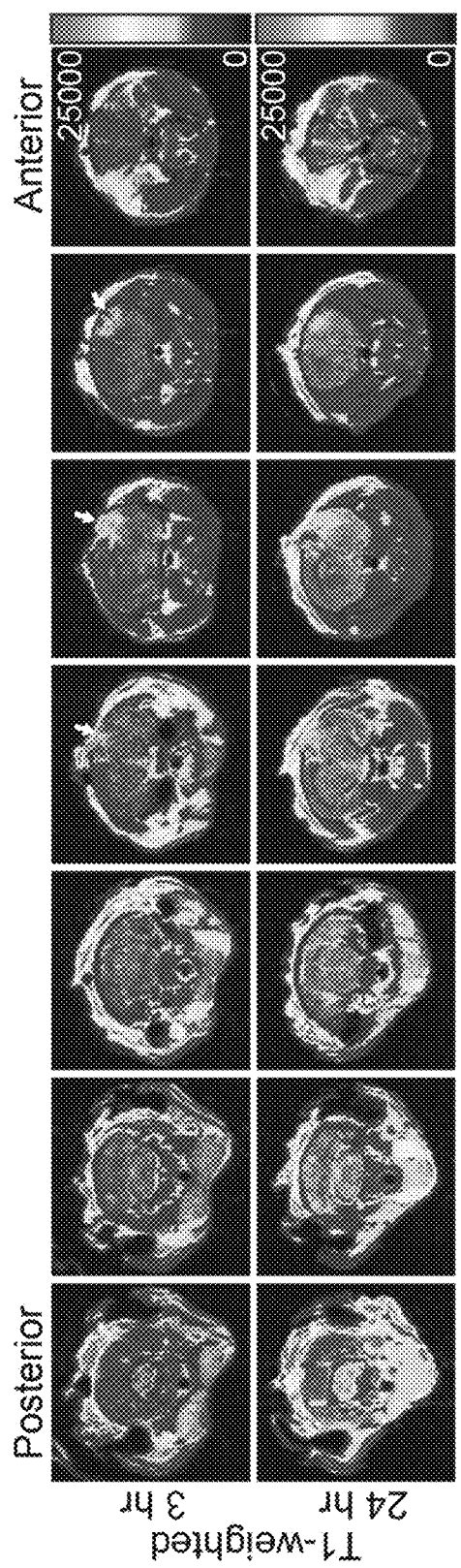
FIGS. 2A-2C illustrate in vivo behavior for a representative ORP when injected immediately after controlled cortical impact (CCI) and magnetic resonance (MR) imaging revealed that the ORP is taken up and retained within damaged brain when administered immediately after CCI-induced TBI.
Figure 2B:
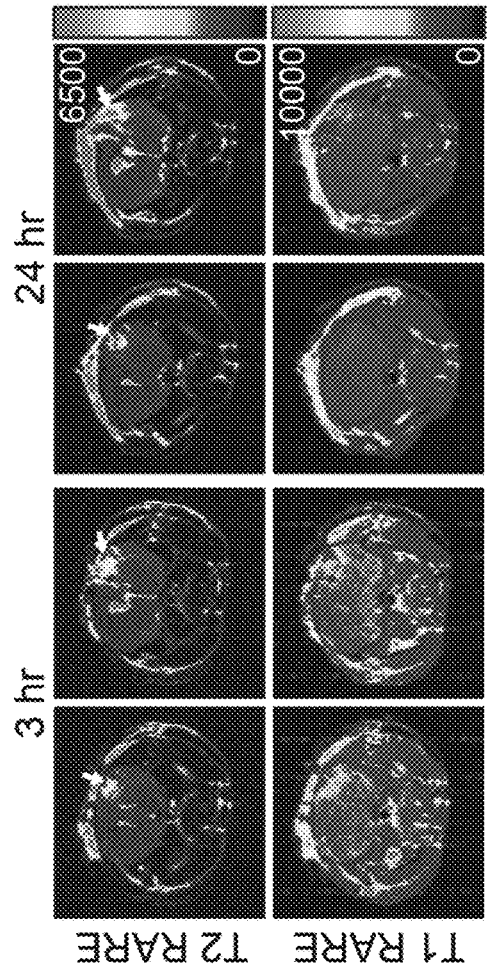
Figure 2C:
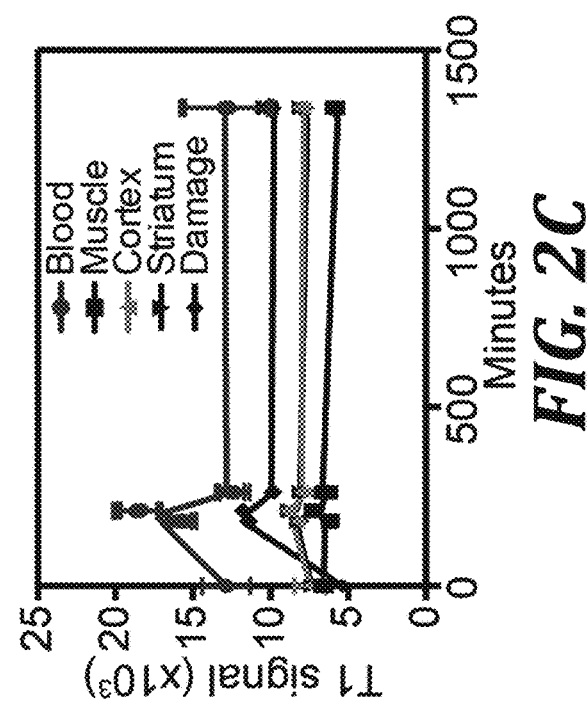

To determine if ORP accumulates in damaged brain, animals were imaged using MRI, where Gd attached to ORP provides contrast in T1-weighted images. Prior to injection, no increase in signal is observed in the damaged region of brain in T1-weighted images, but after injection significant contrast was observed in the damaged region of brain (FIG. 2A). The T1 enhancement caused by ORP is highly similar in distribution to the pattern of edema seen in the T2-weighted images (FIG. 2B). This indicates that ORP accumulates in the damaged region of brain and is retained through an EPR effect. Even after 24 hrs, ORPs persisted in the damaged region as evidenced by enhancement in T1-weighted images at this time point and quantitative analysis of T1 signal intensity (FIG. 2C). Signal increase above background was most pronounced in the blood and damaged region of brain, with slight elevations in T1 signal in the striatum, cortex, and muscle around 3 hrs after ORP injection. T1 signal only remained increased in the damaged region of the brain indicating that while ORP is cleared from circulation, it persists in the region of injury.

ORP Treatment Reduces Neurodegeneration Following TBI

Figure 3:
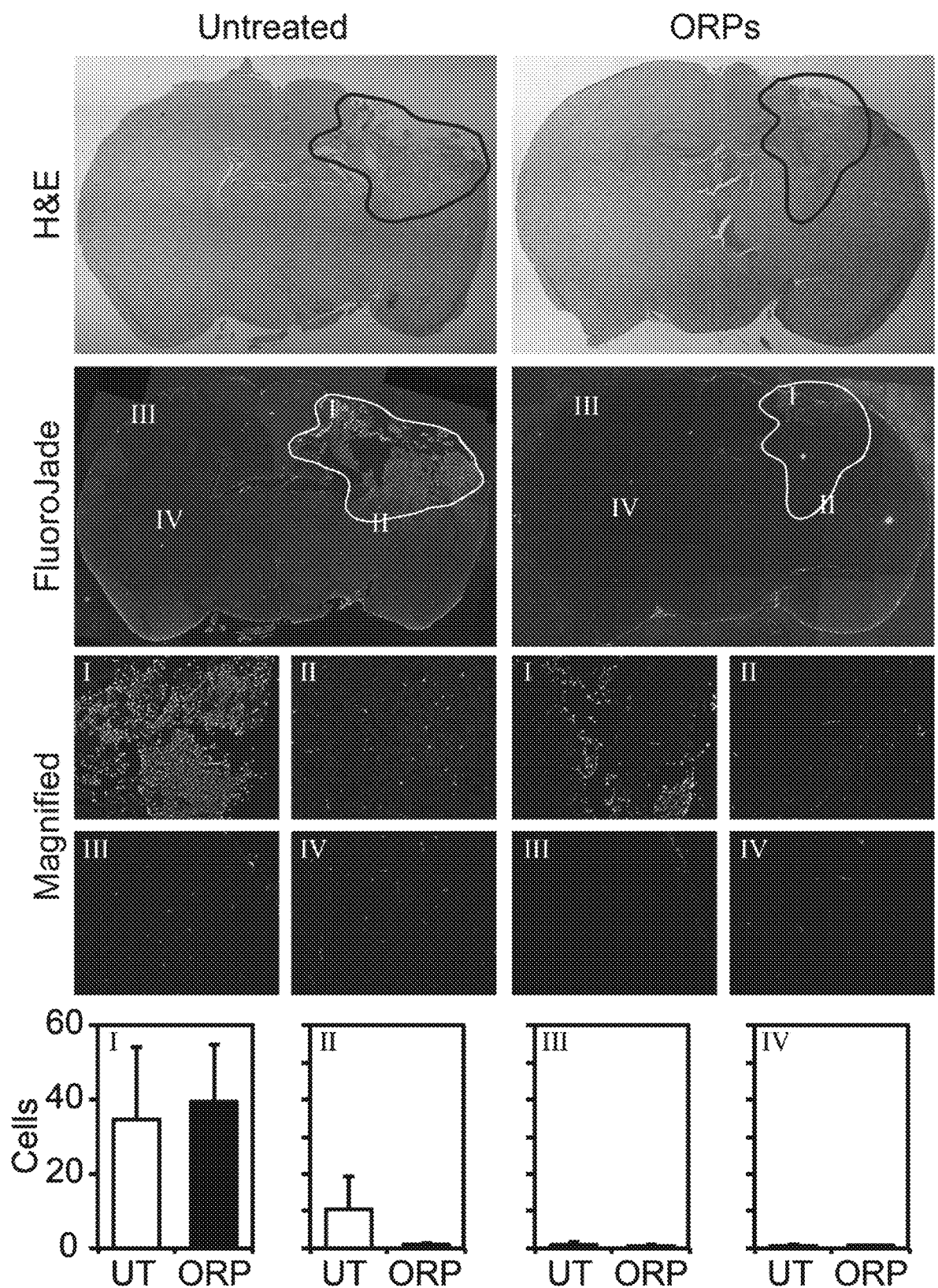
FIG. 3 demonstrates that a representative ORP reduced neurodegeneration in CCI mouse models of TBI. Reduction in neurodegeneration as evidenced by lower FluoroJade C staining in and around the initial injury seen 24 hrs after TBI in mice treated with the ORP (untreated—UT). Damaged neurons were manually counted in each region: (I) at the CCI site, (II) at the deep margin of the CCI site where secondary damage would occur, (III) contralateral cortex, and (IV) contralateral striatum.

To determine if ORP accumulation in damaged brain had an effect on damage to neurons at early time points, brains were collected 24 hrs post-CCI. Sections were stained with FluoroJade C (FJC) and FJC positive cells counted (FIG. 3). The damaged region of brains at the CCI site from untreated and ORP-treated mice showed similar levels of FJC staining, indicating neuronal damage directly caused by the CCI. However, at the deep margin of the CCI site, where an increase in oxidative stress is expected to induce secondary injury, there were significantly fewer FJC positive cells in ORP-treated mice. This suggests the ORPs could sequester excess ROS in and around damaged brain to reduce secondary injury associated early neurodegeneration. There was no difference in FJC staining on the contralateral side of the brain, indicating specificity of this finding to the damaged region.

ORP Treatment Reduces Astrocyte Reactivity in TBI

Figure 4D:
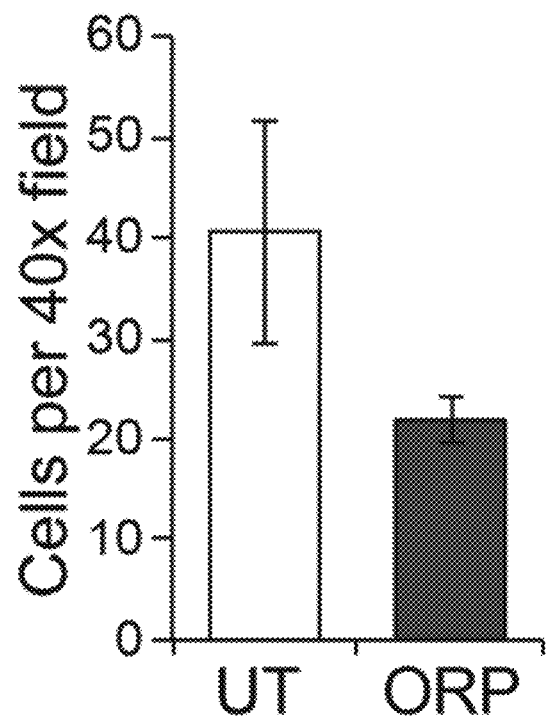
Figure 4E:
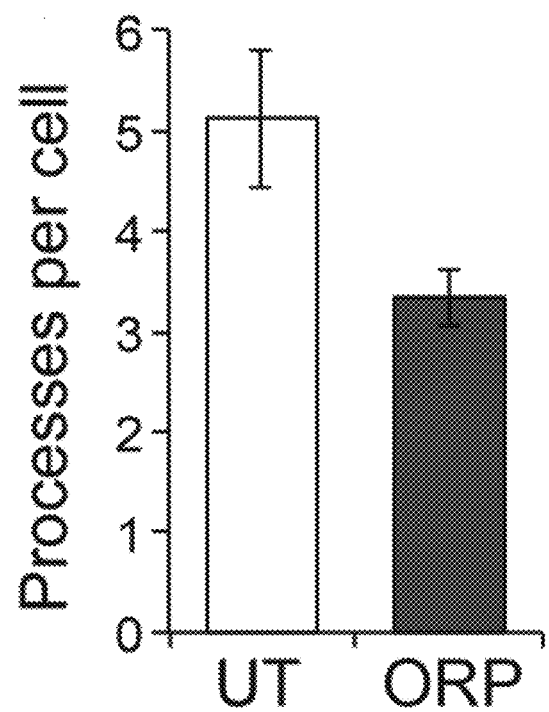

Astrocytes, the most abundant cell in the CNS, are important regulators of neuronal functions as they provide nutrients and recycle neurotransmitters for maintenance of homeostasis within the brain. Secondary damage from TBI is marked by astrogliosis, which can be seen 7 days post-CCI. Increased cell density of astrocytes and greater numbers of astrocytic processes per cell indicate greater extent of gliosis. While reactive gliosis assists to separate injured and uninjured regions in the acute phase of TBI, reactive astrocytes that persist into the chronic phase of the injury can inhibit the integration of newly formed neurons and prevent axon development. Thus, a reduction in reactive astrocytes in damaged brain should promote long-term recovery. Brain sections were stained for the astrocyte marker GFAP, with quantification of cell number and number of processes per cell (FIG. 4). Untreated animals showed a high density of GFAP-positive astrocyte staining near the damaged region, whereas ORP-treated animals showed a lower density of these cells (FIGS. 4A and 4B). Quantification of astrocytes (FIG. 4D) revealed a significantly lower number of astrocytes in brains from ORP-treated animals. Additionally, the astrocytes present near the damaged regions of the brains from the ORP-treated animals had fewer processes (FIGS. 4C and 4E) suggesting lower reactivity. ORP treatment caused a decrease both in GFAP-positive cell number and the number of processes per cell. This suggests ORPs provided a therapeutic effect by sequestering excess ROS and preventing the spread of damage beyond the initial CCI-induced insult.

ORP Treatment Reduces Microglia Activation in TBI

Figure 5B:
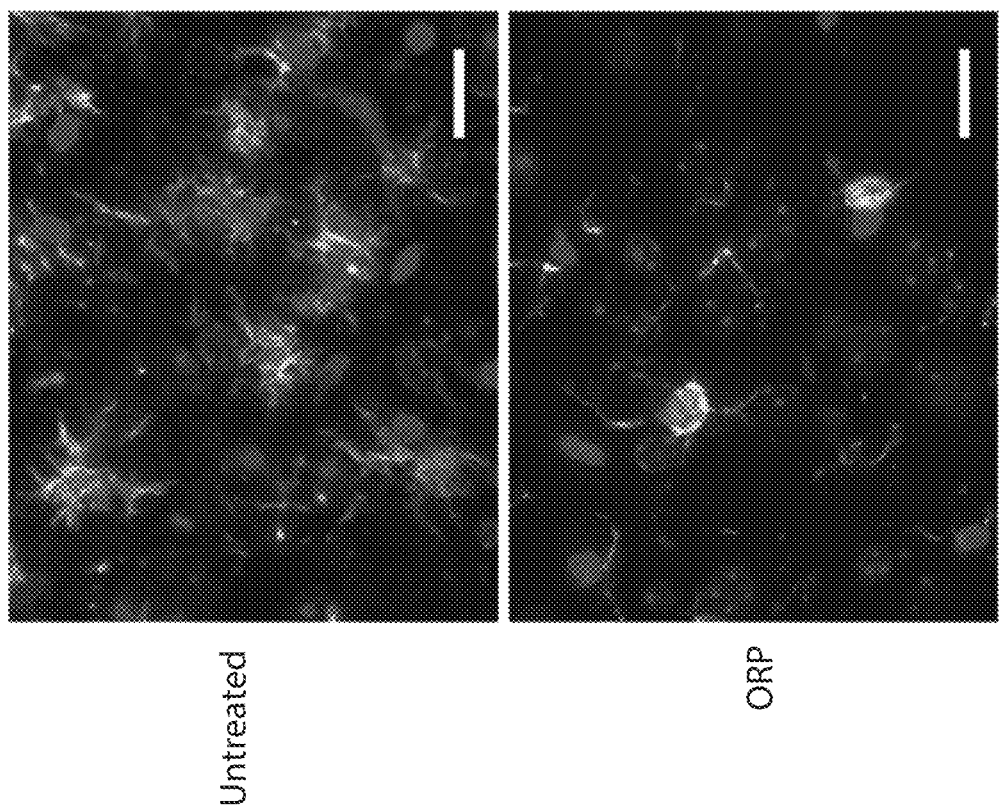
FIGS. 5A-5D illustrate that ORP treatment reduced activated microglia surrounding damage seen 7 days after TBI.
Figure 5A:
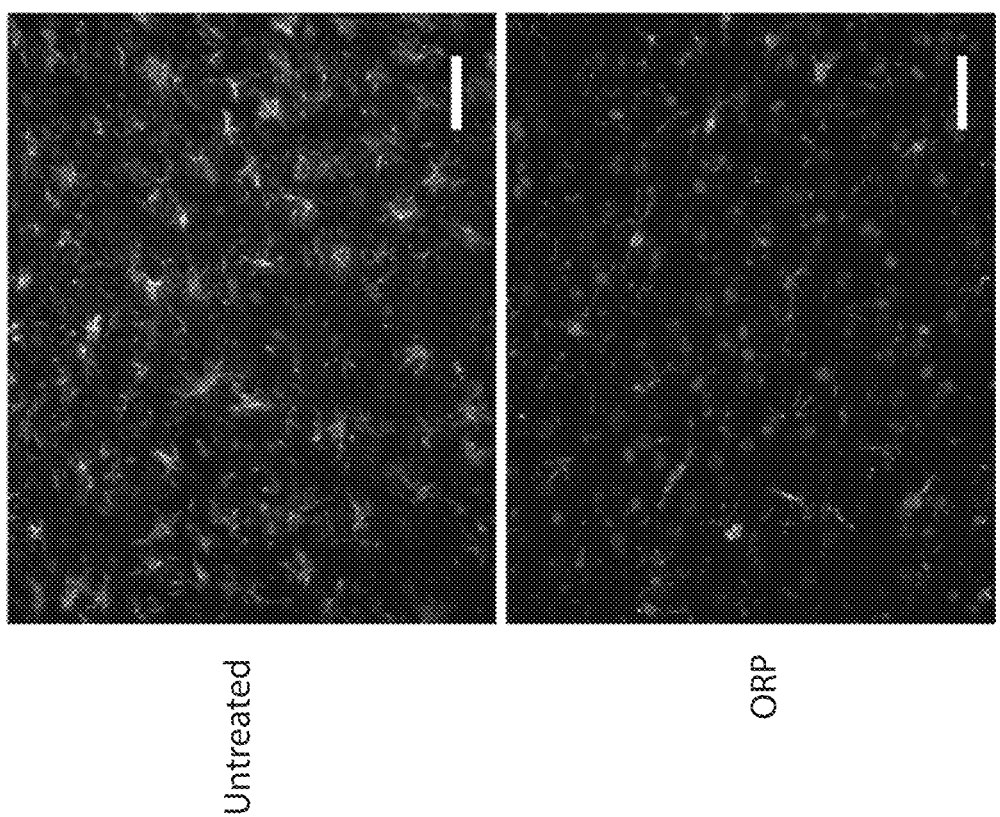
Figure 5C:
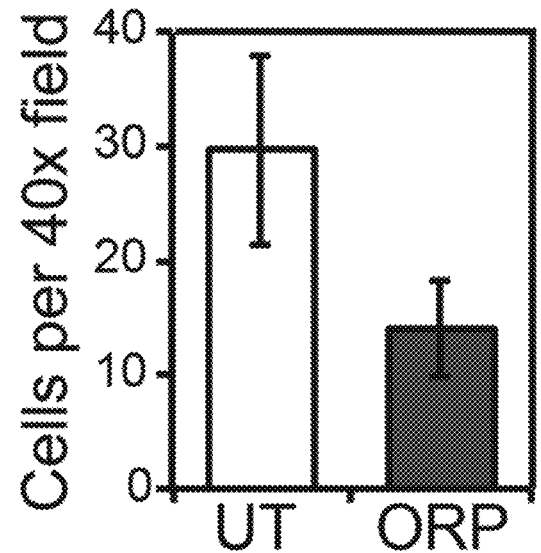
Figure 5D:
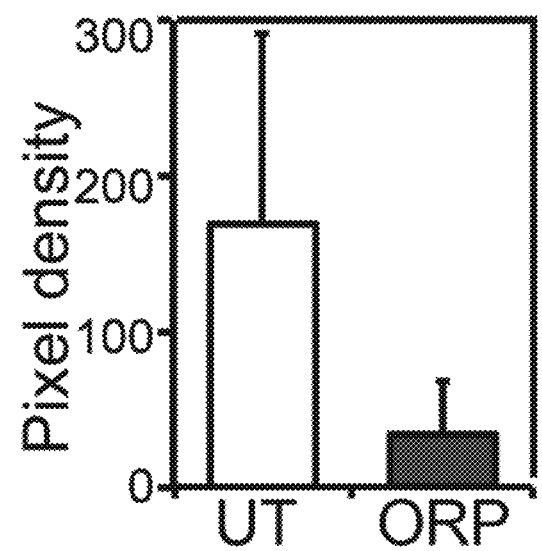

Microglia are activated by the presence of ROS in and around an injured region, and are responsible for waste removal and sequestration of damage. Increased density and greater numbers of microglial processes signify greater gliosis. Brain sections were stained for the microglia marker Iba1 and cell number as well as pixel density were quantified (FIG. 5). Untreated animals showed a high density of Iba1-positive microglia staining near the damaged region, whereas ORP-treated animals showed a lower density of these cells (FIGS. 5A and 5B). Quantification of microglia (FIG. 5C) revealed a significantly lower number of microglia in brains from ORP-treated animals. Additionally, the microglia present near the damaged regions of the brains from the ORP-treated animals appeared less activated with smaller cell bodies and fewer processes (FIG. 5B). Indeed, Iba1-positive pixel density quantification revealed a significantly lower pixel density from the ORP treatment group (FIG. 2D). Thus, in agreement with GFAP immunostaining, ORP treatment decreased Iba1-positive cell number and yielded reduced Iba-1 positive cell activation.

ORP can be Delivered Late and Still Accumulate in TBI

Figure 6A:
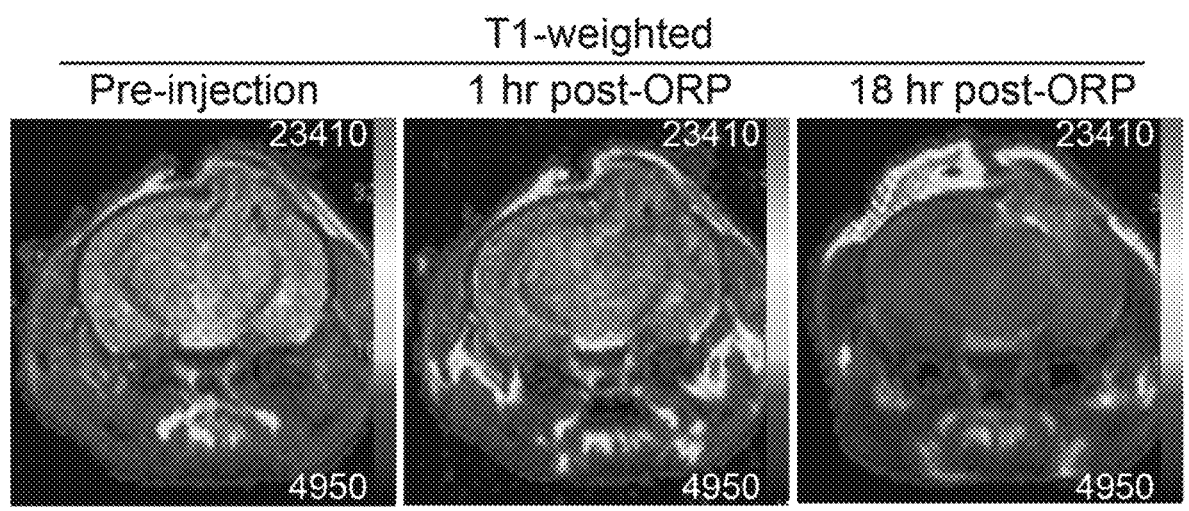
FIGS. 6A-6G illustrate MR imaging and revealed late delivery of a representative ORP 3 hrs post-CCI and retention within damaged brain for at least 24 hrs after treatment.
Figure 6B:
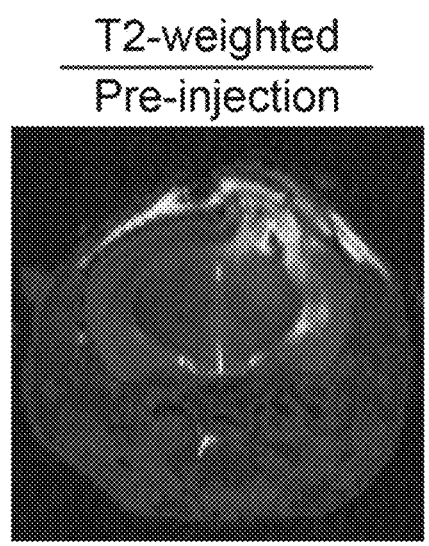
Figure 6C:
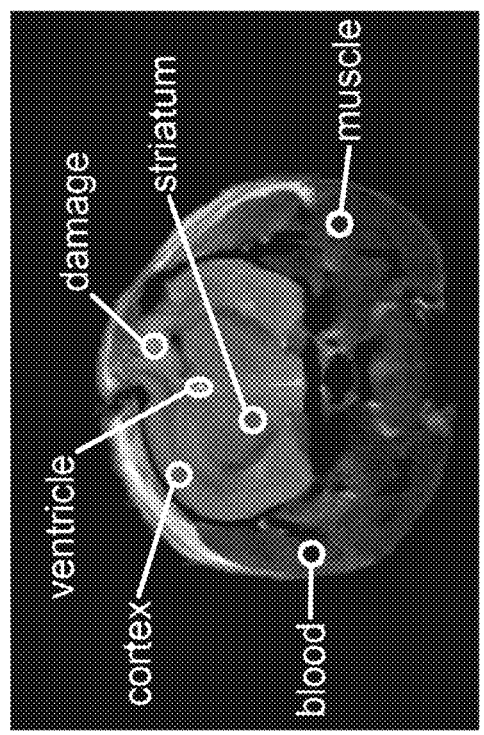
Figure 6C:
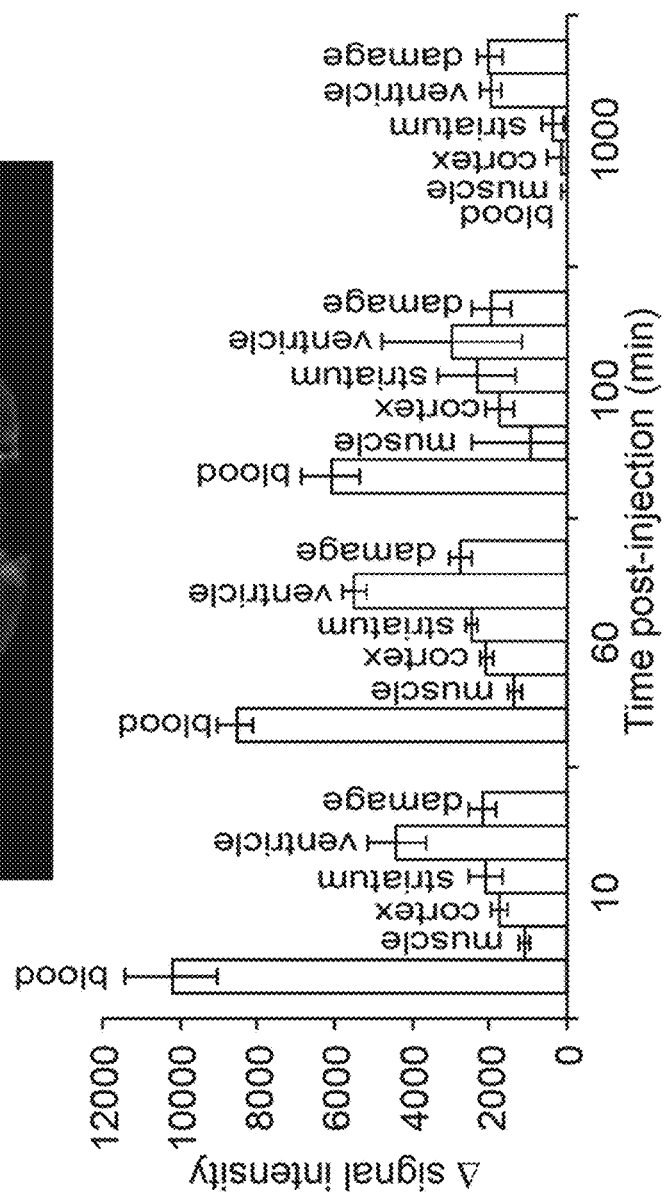
Figure 6D:
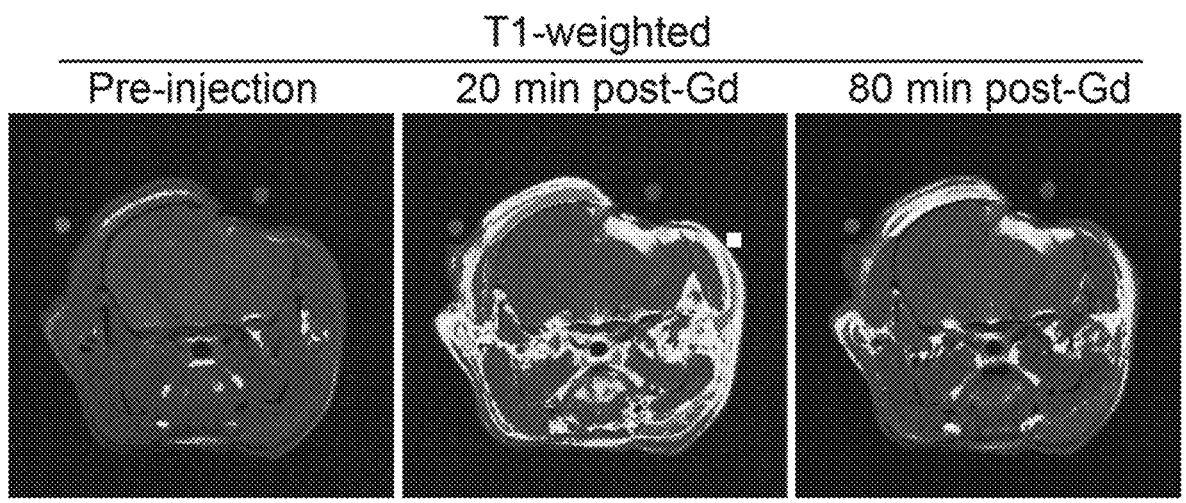
Figure 6E:
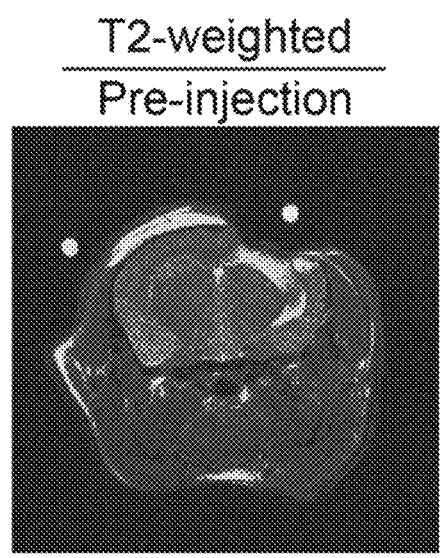
Figure 6F:
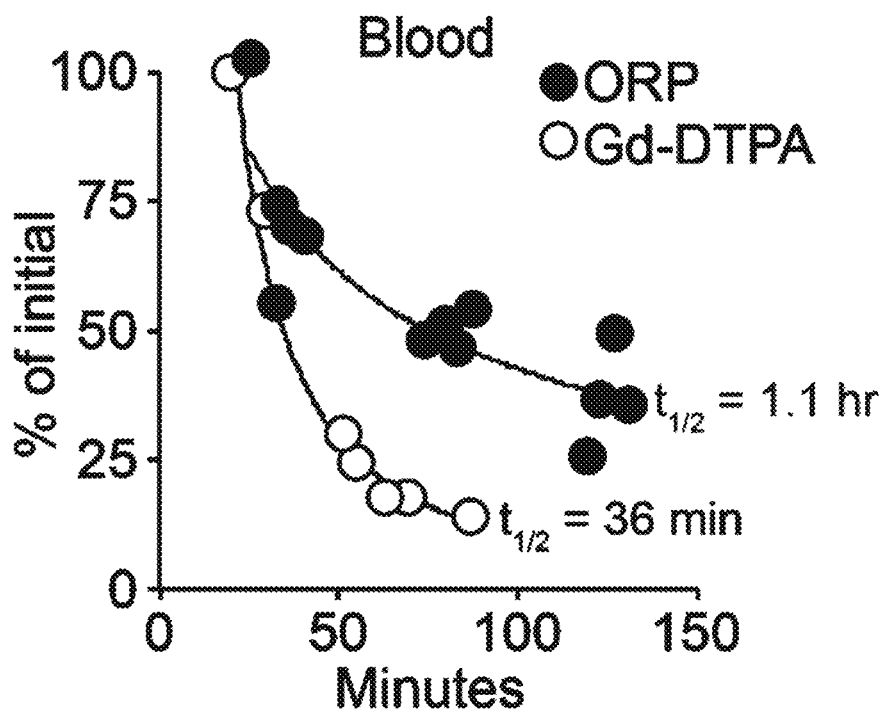
Figure 6G:
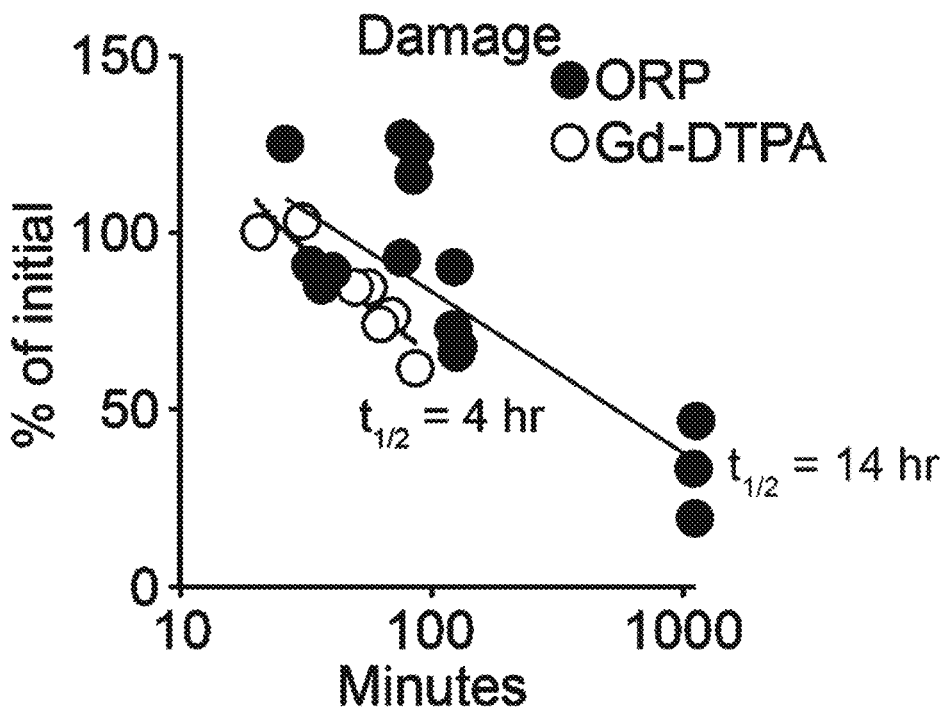

ORP showed accumulation in damaged brain after 18 hrs when injected 3 hrs post-CCI indicating slower uptake kinetics into damaged brain (FIGS. 6A and 6B). This is likely caused by reduced local capillary blood flow in the setting of edema at 3 hrs post-CCI, compared to immediately after CCI (FIG. 2). The timing of TBI treatment is known to be critical for efficacy of some treatments. The results suggest that the window of ORP treatment extends for at least three hours. Despite intravascular administration, ORP was found to accumulate in the ventricles suggesting they are circulating in the CSF and may provide additional protection over a number of days as the half-life in the ventricles was nearly 40 hrs. Some signal enhancement was observed in the muscle, cortex, and striatum, but was eliminated by 24 hrs (FIG. 6C). Animals injected with Magnevist (Gd-DTPA) also displayed contrast enhancement in damaged brain indicating disruption of the BBB (FIG. 6D) throughout the extent of lesion seen on T2-weighted images (FIG. 6E). Clearance of Gd-DTPA was faster than that of ORP, with an ORP blood half-life of about 1.1 hrs compared to a blood half-life of 36 min for Gd-DTPA (FIG. 6F). The half-life of ORP in damaged brain was greater than 14 hrs compared to 4 hrs for Gd-DTPA (FIG. 6G).

The present invention provides methods and compositions that include an oxygen reactive polymer (ORP) that acts as an ROS sponge to sequester excess ROS in and around a TBI. As described herein, the use of RAFT polymerization technology and the exclusive use of commercially available and inexpensive starting materials allows for easy scale up of the copolymers for clinical grade production. The representative ORP showed a greater than 3-fold reduction in $H_2O_2$ levels in vitro showing its high ROS sponge capacity and ability to protect astrocytes from intracellular ROS accumulation. ORP could sequester nearly 30 $H_2O_2$ molecules per single polymer indicating its significant ROS sponge capacity. The hydrodynamic diameter of the representative ORP was 8 nm, an appropriate size to generate efficient EPR effects. The representative ORP was found to accumulated in damaged brain and was retained for at least 18 hrs, likely a result of passive accumulation of ORP.

Significant neuronal damage was observed in the brains of mice receiving CCI-induced TBI. This damage was reduced in brains of mice that received a bolus injection of ORP within 30 min post-CCI induced TBI, suggesting ORP could reduce ROS in and around damaged brain and thus reduce short-term neurodegeneration. Furthermore, this bolus treatment reduced the levels in gliosis observed 7 days following CCI-induced TBI suggesting the reduction in ROS in and around damaged brain reduces the spread of damage. This is significant and is expected to dramatically improve long-term cognitive function and recovery.

The following is provided for the purpose of illustrating, not limiting the invention.

Example

Materials and Methods

Gadolinium (III) 1,4,7,10-tetraazacyclododecane-1,4,7-tris(acetic acid)-10-(4-aminobutyl)acetamide Gd-DO3A-Butylamine (X-287) was purchased from Macrocyclics. All chemicals were purchased from Sigma unless otherwise specified. All cell culture reagents were purchased from Life Technologies unless otherwise specified. Antibodies were purchased from Wako (Richmond, VA, USA).

The Preparation, Characteristics, and Properties of a Representative ORP

In this example, the preparation, characterization, and properties of a representative ORP is described.

Synthesis of poly($MEM_{co}O950_{co}MNHS$)

The RAFT copolymerization of 2-(methylthio)ethyl methacrylate (MEM), polyethyleneglycol monomethylether methacrylate (FW~950 Da) (O950), and methacrylic acid N-hydroxysuccinimide ester (MNHS) was conducted at an initial monomer feed of 70%, 25%, and 5% respectively with 4-cyano-4-(phenylcarbonothioylthio)pentanoic acid (CTP) and 4,4'-azobis(4-cyanovaleric acid) (ABCVA) as the RAFT chain transfer agent and initiator respectively in dixoxane at 70° C. for 18 h. The initial monomer ([M]$_o$:[CTA]$_o$:[I]$_o$) ratio was 100:1:0.2. To a 25 mL round bottom flask was added MEM (1.00 g, 6.24 mmol), O950 (2.12 g, 2.22 mmol), MNHS (82 mg, 0.45 mmol), CTP (24.9 mg, 89 μmol), ABCVA (17.8 mg, 17.83 μmol), and dioxane (12.8 mL). The solution was then purged with nitrogen for 30 minutes and then allowed to heat for 24 h at 70° C. The polymerization solution was then purified via precipitation from a 20 times excess of diethyl ether. The precipitate was then dissolved in acetone and subsequently precipitated once more from diethyl ether. This procedure was repeated six times after which the polymer was dried under high vacuum for 24 hours. The final polymer had a number average molecular weight and dispersity of 35,600 g/mol and 1.09 respectively.

Conjugation of Gd amine to poly($MEM_{co}O950_{co}MNHS$)

To a 10 mL round bottom flask was added poly($MEM_{co}O950_{co}MNHS$) (1.8 g, 0.05 mmol polymer), Gd-DO3A-butylamine (X-287) (0.10 g, mmol), and DIEA (0.100 mL, 1.04 mmol), and DMSO (5.5 mL). The solution was then allowed to react at room temperature for 24 hours.

After this time the solution was purified thrice via dialysis against 4 L of deionized water at 5° C. in Spectra/Por regenerated cellulose membranes (6-8 kDa cutoff). The resultant solution was then further purified via PD10 column (Sephadex G-25 resin). The final dry polymer was then isolated by lyophilization. The concentration of Gd per polymer was determined by inductively coupled plasmon resonance atomic emission spectroscopy (ICP-AES).

DCFH-DA Assay

DCFH-DA (2,7-dichlorodihydrofluorescein diacetate) was dissolved in methanol to make a 1 mM stock solution, which was aliquoted and stored at −80° C. A 50 µM working solution was prepared by diluting in PBS. ORP was dissolved at 100 mg/mL in PBS and diluted with various concentrations of $H_2O_2$ to 10 mg/mL in 630 µL. After 1 hr to allow for ORP to react with ROS, 70 µL of DCFA-DA was added and allowed to react for 20 min before measuring fluorescence (ex: 480, em: 530) on a SpectraMax microplate reader (Molecular Devices). For human astrocyte culture, cells were seeded the day before treatment in 24-well plates at 25,000 cells per well. Prior to exposure to $H_2O_2$, cells were washed with serum free DMEM without sodium pyruvate (ROS medium) after which fresh ROS medium or ROS medium containing 1 mM $H_2O_2$ was added. ORP was then added to the treatment wells and incubated for 30 min. Cells were subsequently washed 3× with PBS, then fresh ROS medium containing 10 µM DCFH-DA reagent added to each well. After a 30 min incubation, cells were washed thrice with PBS, fresh ROS medium added, then imaged by fluorescence microscopy using a Nikon Ri1 Color Cooled Camera System (Nikon Instruments, Melville, NY).

Controlled Cortical Impact (CCI) Mouse Model of TBI 8-10 Week old C57/B6 mice were induced with 4% isoflurane gas via inhalation and maintained at 1.5-2%, then placed upon a warm heating pad set to 100° F. to maintain body temperature. Prior to surgery, hair on the top of the skull was trimmed and epilated via shears and Nair (Church and Dwight Co., Inc., Princeton, NJ). Lidocaine (0.05 mL at a 5 mg/mL) and bupivacaine (0.05 mL at 0.3 mg/mL) were injected subcutaneously under the scalp. After 5 min to allow anesthetic to absorb, a midline incision was made in the skin from lambda to bregma. Fascia and skin were retracted and a small hole drilled using a high speed surgical drill over the left frontoparietal cortex (3 mm anterior and 2 mm left from lambda), and a 3 mm circular cranial window created using rongeurs. A pneumatically-operated controlled cortical impactor (CCI) with a 3 mm convex tip was used to impact the brain normal to the dura surface at a depth of 1 mm at 6 m/s and remained in the brain for 150 ms. Incisions were closed using skin glue and mice given an intraperitoneal injection of buprenorphine (0.1 mg/kg). Mice were monitored under a heat lamp until awake. Within 15 min post-surgery ORP were injected through the tail vein at 100 mg/mL in PBS.

Magnetic Resonance Imaging

In vivo mouse brain MRI was conducted on a 14 Tesla (T) MR scanner (Avance III, Bruker Corp., Billerica, MA) prior to and after administration of ORP to generate serial T1 weighted (T1w) images and T2 weighted (T2w) images. T1w and T2w MRI was performed for a group of two mice approximately 3 hours post-CCI followed by an ORP injection via tail vein (see FIG. 6). Three consecutive T1w images were acquired with RARE (rapid acquisition with refocused echoes) pulse sequence: TR/TE=667.5/4.5 ms, matrix=256×128, field of view (FOV)=25.6×25.6 mm, number of averages (NA)=1, 15 slices and 1 mm slice thickness. Approximately 2 hrs post-CCI, the other group of two mice was used for T1w and T2w MRI before and after the ORP injection via tail vein (see FIG. 6). A series of T1w images were acquired using a fast low angle shot (FLASH) pulse sequence. There were three—four consecutive T1w sequences acquired both pre and post injection—one set of three pre injection acquisitions and then three sets of four post injection acquisitions with an additional set post the following day (4 post imaging total). These images utilized a 3 dimensional (D) FLASH sequence: TR/TE=20/3.87 ms, flip angle=20°, matrix=160×160×30, FOV=25.6×25.6 mm, NA=2, 30 slices and 3D slab of 15 mm. For the first group of mice, T2w images (TR/TE=5500/50 ms) were selected from RARE pulse sequence with (TR=214.3, 500, 1000, 1500, 3000 and 5500 ms and TE=10, 30, 50, 70 and 90 ms, matrix=256×128, FOV=25.6×25.6 mm, NA=1, 2 slices and 1 mm slice thickness. For the second group of mice, T2w images (TR/TE=4000/37.7 ms) were selected from multi-slice and multi-echo imaging conducted with TR/TE=4000/6.3-75.4 ms (12 echoes with 6.3 ms spacing), matrix=256×128, NA=1, 15 slices and 1 mm slice thickness.

Assessment of Neuronal Damage

Brains from mice were collected 1 day and 7 days post-CCI, cut in half at the site of CCI, and fixed in 10% formalin for 48 hrs prior to exchanging to 70% ethanol. Brains were then embedded in paraffin and sectioned. Deparaffinization was performed in two xylene washes, then sections rehydrated in a series of 2 min ethanol washes (100%, 95%, 80%, 70%, 0%). Neuronal damage was visualized using the FluoroJade C reagent (Fisher Scientific) following the manufacturer's protocol. Briefly, slides were immersed in 0.06% $KMnO_4$ for 20 min, followed by a 2 mM water wash, then 0.0001% FluoroJade C in 0.1% acetic acid for 30 mM. Slides were then washed with water thrice, air dried and then cleared in xylene prior to mounting and imaging. Sections were visualized at 40× by fluorescence microscopy using a Nikon Ri1 Color Cooled Camera System, and images stitched together using Photoshop.

Histological Analysis of Gliosis

Brains from mice were collected 1 day and 7 days post-CCI, cut in half at the site of CCI, and fixed in 10% formalin for 48 hrs prior to exchanging to 70% ethanol. Brains were then embedded in paraffin and sectioned. Deparaffinization was performed in two xylene washes, a xylene:ethanol wash, then sections rehydrated in a series of 2 min ethanol washes (100%, 95%, 70%, 50%, 0%). Blocking was performed with PBS containing 10% FBS and 1% sodium azide (PSA) for 2 hrs. Sections were stained with rabbit anti-GFAP polyclonal antibody (Dako, 1:5000 dilution) in PSA overnight at 4° C. After 3 washes with PSA, incubation was resumed with PSA containing FITC-conjugated goat anti-rabbit secondary antibody (Abcam, 1:1000 dilution) for 1 hr at room temperature. Washed brain sections were counterstained with DAPI and mounted onto slides using ProLong Gold antifade reagent (Life Technologies). Cells were visualized at by fluorescence microscopy using a Nikon Ri1 Color Cooled Camera System. For Iba1 immunostaining, after deparaffinization and rehydration antigen retrieval was performed in citrate buffer (10 mM sodium citrate, pH 6.0, 0.1% Tween 20) for 20 min at 95° C., followed by blocking in PSA. Sections were stained using rabbit anti-Iba1 polyclonal antibody (Wako, 1:200 dilution) in PSA overnight at 4° C., and then secondary, counterstaining, and imaging were identical to GFAP immunostaining described above.

While illustrative embodiments have been illustrated and described, it will be appreciated that various changes can be made therein without departing from the spirit and scope of the invention.

The invention claimed is:

1. A method for treating traumatic brain injury, comprising administering a therapeutically effective amount of a copolymer to a subject in need thereof, wherein the copolymer has the formula

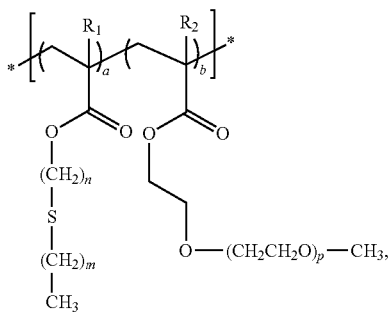

wherein
n is an integer from 1 to 12,
m is an integer from 0 to 12,
p is an integer from 6 to 40,
$R_1$ and $R_2$ are independently selected from hydrogen or methyl,
a is the mole fraction of the repeating unit and is from about 0.25 to about 0.95,
b is the mole fraction of the polyalkylene oxide containing repeating unit and is from about 0.05 to about 0.75;
a+b is 1.0; and
* represents the remainder of the copolymer.

2. The method of claim 1, wherein treating traumatic brain injury comprises reducing neurodegeneration.

3. The method of claim 1, wherein treating traumatic brain injury comprises altering gliosis.

4. The method of claim 1, wherein treating traumatic brain injury comprises treating the secondary effects of traumatic brain injury.

5. The method of claim 1, wherein treating traumatic brain injury comprises treating one or more of reperfusion injury, delayed cortical edema, blood-brain barrier breakdown, local electrolyte imbalance, neurovascular unit dysfunction, and intracranial pressure.

6. The method of claim 1, wherein administering the copolymer comprises intravenous, intranasal, intrathecal/intraventrical, or intracranial administration.

7. The method of claim 1, wherein the copolymer is in the form of a nanoparticle.

8. The method of claim 1, wherein the copolymer is a random copolymer.

9. The method of claim 1, wherein the polymer further comprises a diagnostic group.

10. The method of claim 9, wherein the diagnostic group is a magnetic resonance imaging group, a radiolabel group, a fluorescent group, a luminescent group, an X-ray/CT group, or an ultrasound group.

11. The method of claim 1, wherein the polymer has a hydrodynamic diameter from about 4 to about 100 nm.

12. The method of claim 1, wherein the polymer has a molar mass dispersity from about 1.05 to about 1.30.

13. The method of claim 1, wherein the polymer has a number average molecular weight ($M_n$) from about 5,000 to about 100,000.

14. A copolymer having the formula

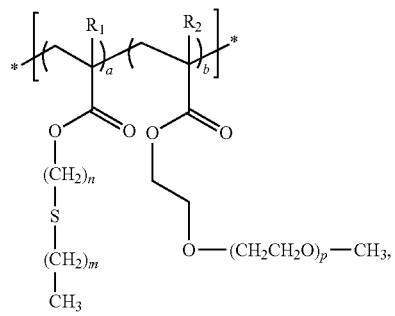

wherein
n is an integer from 1 to 12,
m is an integer from 0 to 12,
p is an integer from 6 to 40,
$R_1$ and $R_2$ are independently selected from hydrogen or methyl,
a is the mole fraction of the repeating unit and is from about 0.25 to about 0.95,
b is the mole fraction of the repeating unit and is from about 0.05 to about 0.75;
a+b is 1.0; and
* represents the remainder of the copolymer.

15. The copolymer of claim 14 in the form of a nanoparticle.

16. The copolymer of claim 14, wherein the copolymer is a random copolymer.

* * * * *